United States Patent
Lulla et al.

(10) Patent No.: US 11,034,959 B2
(45) Date of Patent: Jun. 15, 2021

(54) TREATMENT OF TUMORS WITH MIRNA TARGETING CDK4/CDK6

(71) Applicant: Institute For Cancer Research, Philadelphia, PA (US)

(72) Inventors: Amriti R. Lulla, Philadelphia, PA (US); Wafik S. El-Deiry, Philadelphia, PA (US)

(73) Assignee: Institute For Cancer Research, Philadelphia, PA (US)

( * ) Notice: Subject to any disclaimer, the term of this patent is extended or adjusted under 35 U.S.C. 154(b) by 0 days.

(21) Appl. No.: 16/487,355

(22) PCT Filed: Feb. 26, 2018

(86) PCT No.: PCT/US2018/019649
§ 371 (c)(1),
(2) Date: Aug. 20, 2019

(87) PCT Pub. No.: WO2018/157026
PCT Pub. Date: Aug. 30, 2018

(65) Prior Publication Data
US 2020/0056184 A1    Feb. 20, 2020

Related U.S. Application Data

(60) Provisional application No. 62/463,670, filed on Feb. 26, 2017.

(51) Int. Cl.
| | |
|---|---|
| *A61K 48/00* | (2006.01) |
| *C07H 21/04* | (2006.01) |
| *C12N 15/113* | (2010.01) |
| *A61P 35/00* | (2006.01) |
| *A61K 45/06* | (2006.01) |

(52) U.S. Cl.
CPC .......... *C12N 15/1135* (2013.01); *A61P 35/00* (2018.01); *C12N 15/113* (2013.01); *A61K 45/06* (2013.01); *C12N 2310/141* (2013.01); *C12N 2320/30* (2013.01)

(58) Field of Classification Search
CPC .............. C12N 15/113; C12N 2320/30; C12N 2310/141
See application file for complete search history.

(56) References Cited

U.S. PATENT DOCUMENTS

| | | | |
|---|---|---|---|
| 2015/0087607 A1* | 3/2015 | Marcusson | A61K 48/00 514/27 |
| 2015/0209382 A1 | 7/2015 | Reid et al. | |
| 2016/0317676 A1* | 11/2016 | Hope | A61K 9/1272 |
| 2020/0172984 A1* | 6/2020 | Kozono | C12N 15/113 |
| 2020/0182897 A1* | 6/2020 | Sudo | C12M 1/00 |
| 2020/0255910 A1* | 8/2020 | Kondou | C12Q 1/68 |

OTHER PUBLICATIONS

Malumbres et al., "To cycle or not to cycle: a critical decision in cancer", Nat Rev Cancer, 2001, 1, pp. 222-231.
Russ et al., "The p16(INK4a)/CDKN2A tumor suppressor and its relatives", Biochim. Biophys. Acta, 1998, 1378, pp. F115-F177.
Xiao et al., "Regulation of cyclin-dependent kinase 4 translation through CUG-binding protein 1 and microRNA-222 by polyamines", Mol Biol Cell, 2011, 22, pp. 3055-3069.
Peyressatre et al., "Targeting cyclin-dependent kinases in human cancers: from small molecules to peptide inhibitors", Cancers , 2015, 7, pp. 179-237.
Shapiro, "Cyclin-dependent kinase pathways as targets for cancer treatment", J Clin Oncol, 2006, 24, pp. 1770-1783.
Sherr et al., "Targeting CDK4 and CDK6: From Discovery to Therapy", Cancer Discov, 2016, 6, pp. 353-367.
Hanahan et al., "Hallmarks of Cancer: The Next Generation", Cell, 2011, 144, pp. 646-674.
Jiang et al., "Requirement of Cyclin E-Cdk2 Inhibition in p16(INK4a)-mediated Growth Suppression", Mol Cell Biol, 1998, 18, pp. 5284-5290.
Garber, "The Cancer Drug That Almost Wasn't", Science, 2014, 345, pp. 865-867.
Georgantas et al., "MicroRNA-206 Induces G1 Arrest in Melanoma by Inhibition of CDK4 and Cyclin D", Pigment Cell Melanoma Res, 2014, 27, pp. 275-286.
Shao et al., "Direct repression of the oncogene CDK4 by the tumor suppressor miR-486-5p in non-small cell lung cancer", Oncotarget, 2016, 7, pp. 34011-34021.
Deng et al., "miR-124 radiosensitizes human glioma cells by targeting CDK4", J. Neurooncol, 2013, 114, pp. 263-274.
Anders et al., "A systematic screen for CDK4/6 substrates links FOXM1 phosphorylation to senescence suppression in cancer cells", Cancer Cell, 2011, 20, pp. 620-634.
Wang et al., "FoxM1 expression is significantly associated with cisplatin-based chemotherapy resistance and poor prognosis in advanced non-small cell lung cancer patients", Lung Cancer, 2013, 79, pp. 173-179.
Cao et al., "18.beta.-glycyrrhetinic acid suppresses gastric cancer by activation of miR-149-3p-Wnt.1 signaling", Oncotarget, 2016, 7(44), pp. 71960-71973.
Sohn et al., "Upregulation of miRNA3195 and miRNA374b Mediates the Anti-Angiogenic Properties of Melatonin in Hypoxic PC-3 Prostate Cancer Cells", J Cancer, 2015, 6(1), pp. 19-28.

* cited by examiner

Primary Examiner — Amy H Bowman
(74) Attorney, Agent, or Firm — Stradley Ronon Stevens & Young, LLP

(57) ABSTRACT

The present disclosure provides miRNA mimics targeting CDK4 and/or CDK6, and compositions comprising the same. Methods for the treatment of tumors, including but not limited to colon cancer, comprising administering a modified oligonucleotide comprising a miRNA are also disclosed herein.

8 Claims, 29 Drawing Sheets

Specification includes a Sequence Listing.

Table 1. Family of miRNAs targeting CDK4

| miRNA | Total | Putative binding sites | | | Context score |
|---|---|---|---|---|---|
| | | 8mer | 7mer-m8 | 7mer-1A | |
| miR-6883-5p | 1 | 1 | - | - | -0.60 |
| miR-149* | 1 | 1 | - | - | -0.58 |
| miR-6785-5p | 1 | 1 | - | - | -0.59 |
| miR-4728-5p | 1 | 1 | - | - | -0.58 |

Table 2. Family of miRNAs targeting CDK6

| miRNA | Total | Putative binding sites | | | Context score |
|---|---|---|---|---|---|
| | | 8mer | 7mer-m8 | 7mer-1A | |
| miR-6883-5p | 2 | - | - | 2 | -0.02 |
| miR-149* | 2 | - | - | 2 | -0.02 |
| miR-6785-5p | 2 | - | - | 2 | -0.02 |
| miR-4728-5p | 2 | - | - | 2 | -0.02 |

Figure 1B

```
hsa-miR-6883-5p   AGGGAGGG-UGUGGUAUCGAUGU--   22
hsa-miR-149-3p    AGGGAGGG-ACCGG--GGCUGUGC    21
hsa-miR-6785-5p   UGGGAGGG-CGUGG-AUGAUCGUC--  22
hsa-miR-4728-5p   UGGGAGGGAGGAGCCAGCAAGCA--   23
                          *****         **
```

TREATMENT OF TUMORS WITH MIRNA TARGETING CDK4/CDK6

FIELD

The present disclosure is directed, in part, to compositions and methods and for the treatment of tumors and cancer, wherein the methods comprise administering a modified oligonucleotide comprising a miRNA targeting CDK4 and/or CDK6.

BACKGROUND miRNAs are 18-22 nucleotide small non-coding RNAs that can inhibit translation and/or affect mRNA stability by binding to the 3' untranslated region (UTR) of their target genes (Ameres et al., Nat. Rev. Mol. Cell Biol., 2013, 14, 475-88; and Friedman et al., Genome Res., 2009, 19, 92-105). Studies in different tumor models have shown that miRNAs can either be oncogenic, as in the case of miR-155, miR-21 and miR17-92 cluster, or tumor suppressors, such as miR-34a, let-7 family and miR-143 (Iorio et al., Cancer J., 2012, 18, 215-22; and Oom et al., Biomed. Res. Int., 2014, 2014, 959461).

There were an estimated 134,490 cases of colorectal cancer (CRC) diagnosed in the U.S. in 2016 and an estimated 49,190 deaths according to the National Cancer Institute (NCI) Surveillance, Epidemiology, and End Results (SEER) program, and the 5-year survival for advanced (stage IV) disease remains low at 13.5% (Howlader et al. (eds), SEER Cancer Statistics Review, National Cancer Institute, Bethesda, Md., 1975-2016). New treatments are needed to address the mortality and morbidity from advanced CRC.

The p16-CDK4/6-Rb pathway is an important target in oncology as it is a central regulator of the mammalian cell cycle in the G1-phase (Malumbres et al., Nat. Rev. Cancer, 2001, 1, 222-31; Ruas et al., Biochim Biophys. Acta, 1998, 1378, F115-77; and Xiao et al., Mol. Biol. Cell, 2011, 22, 3055-69). CDK4 and 6 are important targets in cancer and small molecule inhibitors have been development and some have been approved by the Food and Drug Administration (FDA) as cancer therapeutics (Peyressatre et al., Cancers (Basel), 2015, 7, 179-237; Shapiro, J. Clin. Oncol., 2006, 24, 1770-83; and Sherr et al., Cancer Discov., 2016, 6, 353-67).

Dysregulation of genes in the CDK4/6-Rb cell cycle pathway is an indicator of cancer (Hanahan et al., Cell, 2011, 144, 646-74). Cancer cells subvert different cell cycle checkpoints to continue unchecked growth and proliferation. These mechanisms of overcoming cell cycle checkpoints are mutually exclusive and can involve loss of tumor-suppressor proteins such as p16 INK4A or Retinoblastoma (Rb) or amplification of oncogenes like CDK4, CDK6, Cyclin D. Compared to loss of Rb, inactivation of p16INK4A by homologous deletion, frameshift mutations or methylation are more common events (Ruas et al., Biochim Biophys. Acta, 1998, 1378, F115-77; and Jiang et al., Mol. Cell. Biol., 1998, 18, 5284-90). Loss of p16INK4A permits escape from senescence and provides an advantage for tumor progression. Further, this leaves cancer cells with increased levels of CDK4, CDK6 and Cyclin D-dependent kinase activities. Tumors like melanoma and CRC, however, show amplification of CDK4 and/or CDK4R24C mutations (loss of INK4 binding site). Hence, ongoing clinical trials for CRC patients with advanced disease are evaluating the efficacy small molecule inhibitors of CDK4/6 as single agents and in combination with chemotherapy. Emergent knowledge with CDK4/6 inhibitors in clinical trials indicates that these therapies have limitations as monotherapy (Garber, Science, 2014, 345, 865-7). Thus, there is certainly need to develop alternate strategies to target CDK4/6 and identify biomarkers of response, which is critical for understanding the clinical results seen with CDK inhibitors.

miRNA mimics are emerging therapeutics that can target multiple oncogenes and thus have broad mechanisms of anti-cancer effects. Further, they can serve as biomarkers of response and help predict response.

SUMMARY

In the present disclosure, novel miRNAs that target CDK4/6 and which may be used for therapeutic purposes have been identified. A family of four miRNAs that target CDK4 and CDK6 and lead to anti-proliferative effects in CRC cell lines is described herein. In addition, synergies with, for example, irinotecan and 5-fluorouracil, drugs used to treat CRC in the clinic, have been observed.

The present disclosure provides modified oligonucleotides consisting of 15 to 40 linked nucleobases, or a salt thereof, wherein the oligonucleotide comprises a nucleobase sequence that is at least 80% identical to a nucleobase sequence of hsa-miR-6883-5p, hsa-miR-149-3p, hsa-miR-6785-5p, or hsa-miR-4728-5p.

The present disclosure also provides pharmaceutical compositions comprising any one or more of the modified oligonucleotides described herein which consist of 15 to 40 linked nucleosides, or a salt thereof, wherein the oligonucleotide comprises a nucleobase sequence that is at least 80% identical to a nucleobase sequence of hsa-miR-6883-5p, hsa-miR-149-3p, hsa-miR-6785-5p, or hsa-miR-4728-5p.

The present disclosure also provides methods for treating tumors or cancer comprising administering to a subject in need thereof any one or more of the oligonucleotides described herein, which consist of 15 to 40 linked nucleobases, or a salt thereof, and/or a pharmaceutical agent that induces the production of the one or more oligonucleotides and/or induces PER1 expression, wherein the oligonucleotide comprises a nucleobase sequence that is at least 80% identical to a nucleobase sequence of hsa-miR-6883-5p, hsa-miR-149-3p, hsa-miR-6785-5p, or hsa-miR-4728-5p.

The present disclosure also provides methods for treating tumors or cancer comprising administering to a subject in need thereof a pharmaceutical composition comprising any one or more of the oligonucleotides described herein, which consist of 15 to 40 linked nucleobases, or a salt thereof, and/or a pharmaceutical agent that induces the production of the one or more oligonucleotides and/or induces PER1 expression, wherein the oligonucleotide comprises a nucleobase sequence that is at least 80% identical to a nucleobase sequence of hsa-miR-6883-5p, hsa-miR-149-3p, hsa-miR-6785-5p, or hsa-miR-4728-5p.

These and other embodiments of the present disclosure will become apparent in conjunction with the figures, description and claims that follow.

BRIEF DESCRIPTION OF THE DRAWINGS

FIGS. 1A, 1B, 1C, and 1D show: RNA expression data from TCGA CRC patient samples showing expression of CDK4 and CDK6 in 50 tumor and normal samples (FIG. 1A); TargetScan analysis of putative binding site(s) of family of four miRNAs in the 3'UTR regions of CDK4 and CDK6, respectively (FIG. 1B); scatter plot of expression of miR-149* in 11 CRC patient tumors compared to matched normal tissue (FIG. 1C, left panel); histogram of CDK4/6, p16 and Rb status in the same 11 patients (FIG. 1C, right panel); and a box plot of the $\log_{10}$ RNA expression of PER1 genes in the same 50 normal samples compared to tumor samples (FIG. 1D).

DESCRIPTION OF EMBODIMENTS

Figure 1A:
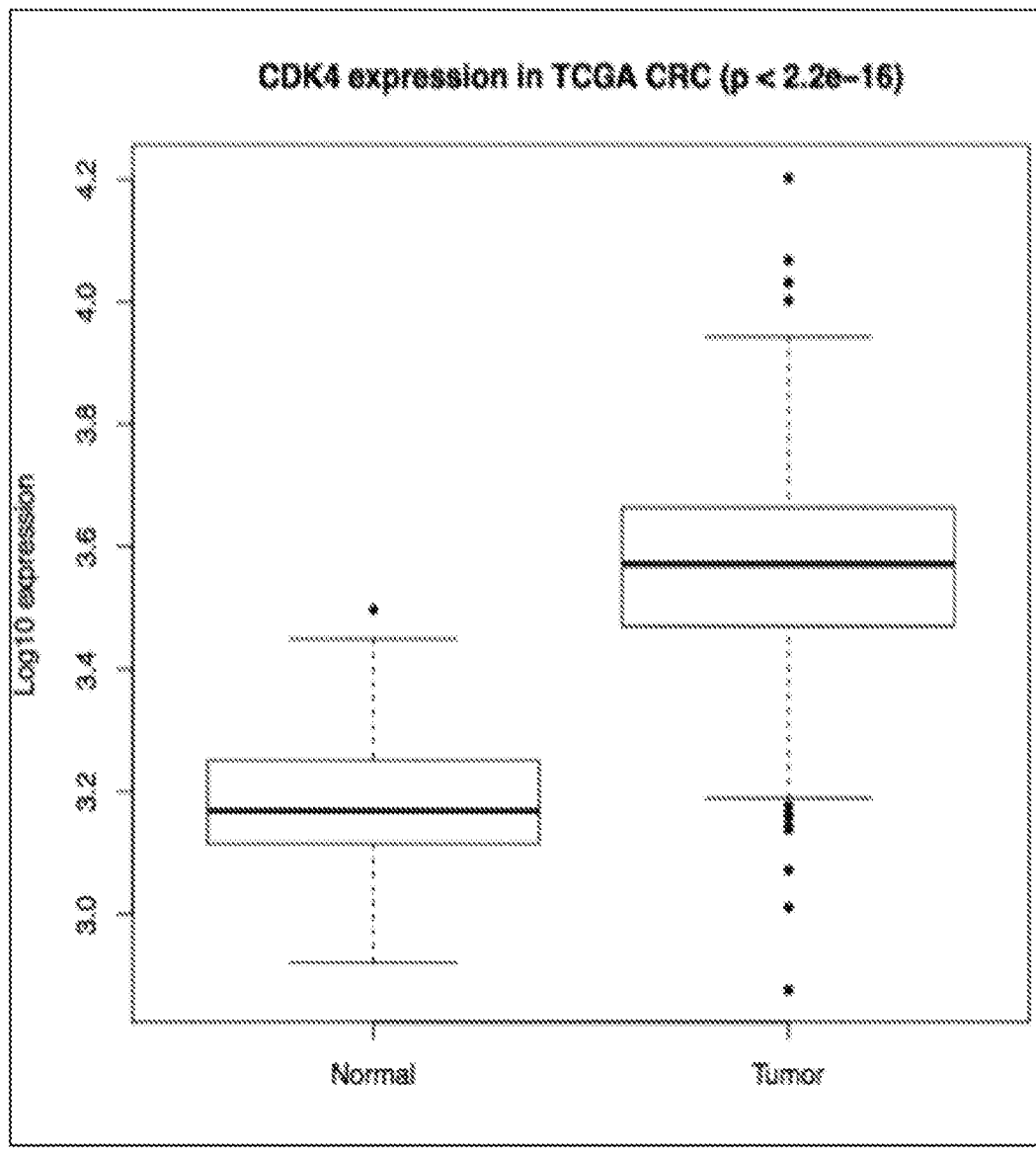
Figure 1A:
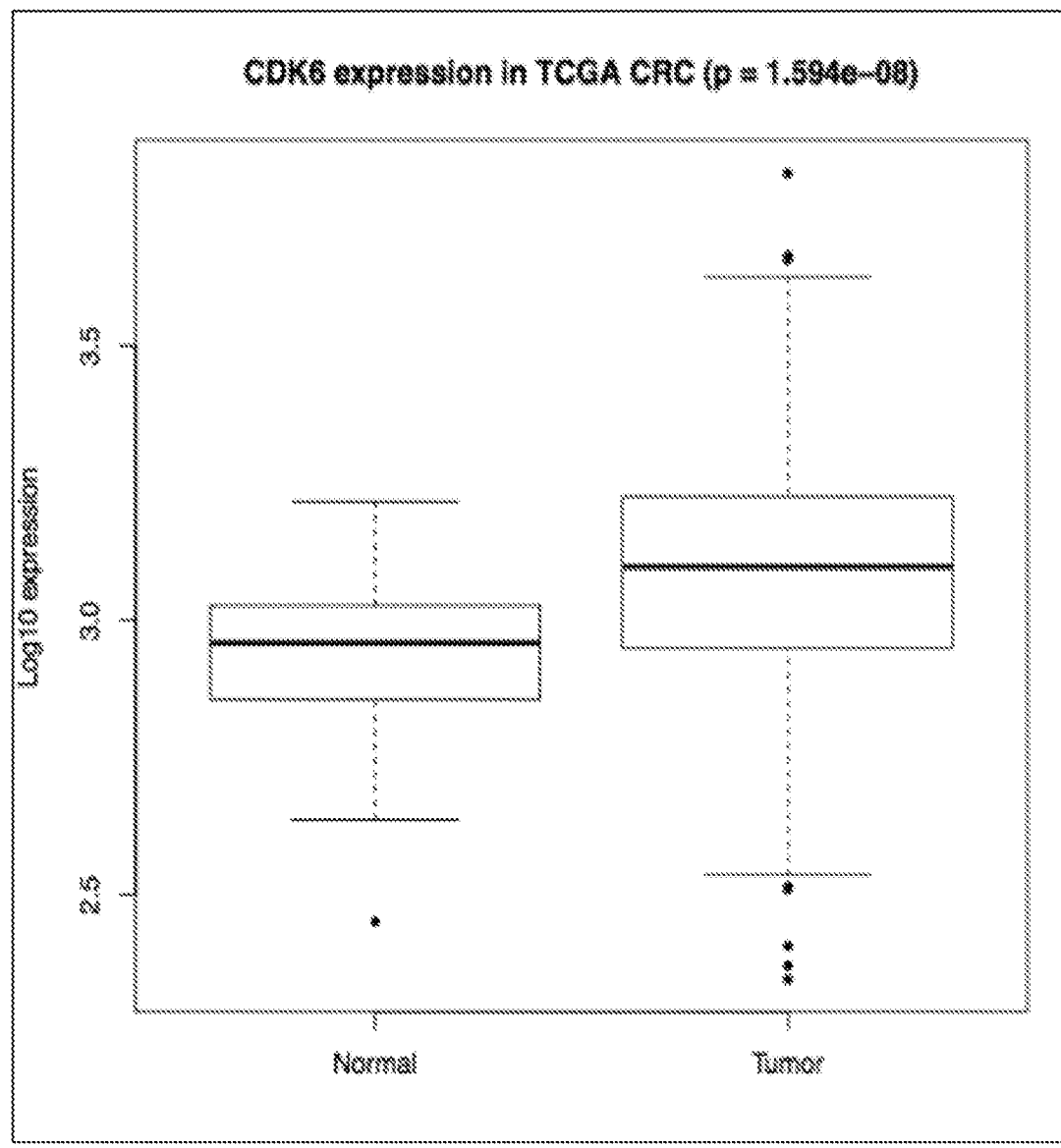

In the present disclosure, computational and TCGA analyses was performed to identify novel miRNAs that can target CDK4/6 and that can be used for therapeutic treatment of colorectal cancer (CRC). The 3'-UTR of CDK4/6 mRNA is shown here to be novel targets of a previously uncharacterized family of miRNAs encompassing miR-6883-5p, miR-149*, miR-6785-5p, and miR-4728-5p. The data presented herein of miRs 6883-5p and 149* revealed that both miRNAs downregulate CDK4 and CDK6 protein and mRNA expression when ectopically expressed in human CRC cell lines. RNA-seq data indicated an inverse relationship between the expression of CDK4/6 and miR-149* and intronic miRNA-6883-5p encoding gene PER1 in CRC patient samples. Restoring expression of miRs 6883-5p and 149* had significant anti-proliferative effects, G0/G1-arrest, and apoptosis in CRC cell lines. Targeting of CDK4/6 by miR-6883-5p and miR-149* can only, in part, explain the anti-proliferative effects of these miRNAs as seen on silencing CDK4/6 in CRC cell lines. Lastly, both miRNAs synergized with frontline CRC chemotherapy irinotecan and sensitized mutant p53 cell lines to 5-FU. Thus, the miRNA-based therapeutic strategy to target CDK4/6 can be used as both a single agent and combinatorial therapy, and to identify biomarkers of response.

In particular, in the present disclosure, a combination of in silico prediction algorithms and TCGA analysis was used to identify tumor suppressor miRNAs that can translate to single agent and/or combinatorial therapies for CRC. There have been previous studies describing miRNAs regulating of CDK4 expression in melanoma and NSCLC (Georgantas et al., Pigment Cell Melanoma Res., 2014, 27, 275-86; Lin et al., Cancer Res., 2010, 70, 9473-82; Shao et al., Oncotarget, 2016, 7, 34011-21; and Deng et al., J. Neurooncol., 2013, 114, 263-74). However, there are no such tumor suppressor miRs identified in CRC and/or studies evaluating their use as therapeutics. In the present disclosure, a new family of miRNAs, whose expression is lost in CRC, has be identified. The primary gene network (i.e., G1-S phase of cell cycle, which is regulated by two of the four miRNAs in the family) was characterized herein. Within the CDK4/6-Rb pathway, the present disclosure presents data that gene targets mediating the anti-proliferative effects of miR-6883-5p and miR-149* include CDK4, CDK6 and FOXM1, which has recently been identified to be phosphorylated by CDK4/6 (Anders et al., Cancer Cell, 2011, 20, 620-34). FOXM1 is a Forkhead Box family transcription factor that has also been also linked to resistance to different chemotherapies like cisplatin and 5-FU (Wang et al., Lung Cancer, 2013, 79, 173-9) and is an important oncogenic target in preclinical development. Thus, the inhibition of CDK4/6 and its downstream effector FOXM1 by miRNAs has an advantage of targeting the CDK4/6-Rb pathway at different levels. The combination experiments with FDA-approved chemotherapies Irinotecan and 5-FU, as demonstrated herein, show that both the miRNAs can sensitize CRC cell lines to each of the drugs and indicate that the use of combinations of miRNAs as adjuvant therapeutics for the treatment of colorectal cancer is a viable clinical strategy. In addition to cell cycle, the pro-apoptotic functions of miR-6883-5p and miR-149* has been demonstrated herein. Both miRNAs, by downregulating anti-apoptotic proteins BCLxL and XIAP, lead to apoptosis both as single and combination in CRC cell lines.

In summary, new miRNAs, including miR-6883-5p and miR-149*, have been identified herein as direct negative regulators of CDK4 and CDK6. Restoring the expression of miR-6883-5p and miR-149* in cancer cells showed antiproliferative effects and apoptosis as single agents and in combination, respectively. Thus, miRNA mimics as adjuvant therapy for cancer is an alternate to small molecule inhibitors.

Unless defined otherwise, all technical and scientific terms used herein have the same meaning as is commonly understood by one of skill in the arts to which the claimed subject matter.

As used herein, the singular forms "a," "an" and "the" include plural referents unless the context clearly dictates otherwise.

As used herein, "colon cancer" means malignancy of the colon, either a primary cancer or metastasized cancer.

As used herein, "subject" means a human or non-human animal selected for treatment or therapy.

As used herein, "in need thereof" means a subject identified as in need of a therapy or treatment. In some embodiments, a subject has a tumor or cancer, such as colon cancer. In such embodiments, a subject has one or more clinical indications of a tumor or cancer, such as colon cancer, or is at risk for developing a tumor or cancer, such as colon cancer.

As used herein, "administering" means providing a pharmaceutical agent or composition to a subject, and includes, but is not limited to, administering by a medical professional and self-administering.

As used herein, "parenteral administration," means administration through injection or infusion. Parenteral administration includes, but is not limited to, subcutaneous administration, intravenous administration, or intramuscular administration.

As used herein, "subcutaneous administration" means administration just below the skin.

As used herein, "intravenous administration" means administration into a vein.

As used herein, "intratumoral administration" means administration within a tumor.

As used herein, "intraperitoneal administration" means administration into the peritoneum (i.e., body cavity).

As used herein, "chemoembolization" means a procedure in which the blood supply to a tumor is blocked surgically, mechanically, or chemically and chemotherapeutic agents are administered directly into the tumor.

As used herein, "duration" means the period of time during which an activity or event continues. In some embodiments, the duration of treatment is the period of time during which one or more doses of a pharmaceutical agent or pharmaceutical composition are administered.

As used herein, "therapy" means a disease treatment method. In some embodiments, therapy includes, but is not limited to, chemotherapy, surgical resection, and/or chemoembolization.

As used herein, "treatment" means the application of one or more specific procedures used for the cure or amelioration of a disease. In some embodiments, the specific procedure is the administration of one or more pharmaceutical agents.

As used herein, "amelioration" means a lessening of severity of at least one indicator of a condition or disease. In some embodiments, amelioration includes a delay or slowing in the progression of one or more indicators of a condition or disease. The severity of indicators may be determined by subjective or objective measures which are known to those skilled in the art.

As used herein, "prevention" refers to delaying or forestalling the onset or development or progression of a condition or disease for a period of time, including weeks, months, or years.

As used herein, "therapeutic agent" means a pharmaceutical agent used for the cure, amelioration or prevention of a disease.

As used herein, "chemotherapeutic agent" means a pharmaceutical agent used to treat cancer.

As used herein, "chemotherapy" means treatment of a subject with one or more pharmaceutical agents that kills cancer cells and/or slows the growth of cancer cells.

As used herein, "dose" means a specific quantity of a pharmaceutical agent provided in a single administration. A dose may be administered in two or more boluses, tablets, or injections. In some embodiments, a dose may be administered in two or more injections to minimize injection site reaction in an individual.

As used herein, "dosage unit" means a form in which a pharmaceutical agent is provided. In some embodiments, a dosage unit is a vial containing lyophilized oligonucleotide. In some embodiments, a dosage unit is a vial containing reconstituted oligonucleotide.

As used herein, "therapeutically effective amount" refers to an amount of a pharmaceutical agent that provides a therapeutic benefit to an animal.

As used herein, "pharmaceutical composition" means a mixture of substances suitable for administering to a subject that includes a pharmaceutical agent. For example, a pharmaceutical composition may comprise a modified oligonucleotide and a sterile aqueous solution.

As used herein, "pharmaceutical agent" means a substance that provides a therapeutic effect when administered to a subject.

As used herein, "active pharmaceutical ingredient" means the substance in a pharmaceutical composition that provides a desired effect.

As used herein, "metastasis" means the process by which cancer spreads from the place at which it first arose as a primary tumor to other locations in the body. The metastatic progression of a primary tumor reflects multiple stages, including dissociation from neighboring primary tumor cells, survival in the circulation, and growth in a secondary location.

As used herein, "overall survival time" means the time period for which a subject survives after diagnosis of or treatment for a disease.

As used herein, "progression-free survival" means the time period for which a subject having a disease survives, without the disease getting worse. In some embodiments, progression-free survival is assessed by staging or scoring the disease. In some embodiments, progression-free survival of a subject having colon cancer is assessed by evaluating tumor size, tumor number, and/or metastasis.

As used herein, "improved colon function" means the change in colon function toward normal limits.

As used herein, "acceptable safety profile" means a pattern of side effects that is within clinically acceptable limits.

As used herein, "side effect" means a physiological response attributable to a treatment other than desired effects. In some embodiments, side effects include, without limitation, injection site reactions, colon function test abnormalities, renal function abnormalities, liver toxicity, renal toxicity, central nervous system abnormalities, and myopathies. Such side effects may be detected directly or indirectly.

As used herein, "injection site reaction" means inflammation or abnormal redness of skin at a site of injection in an individual.

As used herein, "subject compliance" means adherence to a recommended or prescribed therapy by a subject.

As used herein, "comply" means the adherence with a recommended therapy by a subject.

As used herein, "recommended therapy" means a treatment recommended by a medical professional for the treatment, amelioration, or prevention of a disease.

As used herein, "targeting" means the process of design and selection of nucleobase sequence that will hybridize to a target nucleic acid and induce a desired effect.

As used herein, "targeted to" means having a nucleobase sequence that will allow hybridization to a target nucleic acid to induce a desired effect. In some embodiments, a desired effect is reduction of a target nucleic acid.

As used herein, "modulation" means to a perturbation of function or activity. In some embodiments, modulation means an increase in gene expression. In some embodiments, modulation means a decrease in gene expression.

As used herein, "expression" means any functions and steps by which a gene's coded information is converted into structures present and operating in a cell.

As used herein, "nucleobase sequence" means the order of contiguous nucleobases, in a 5' to 3' orientation, independent of any sugar, linkage, and/or nucleobase modification.

As used herein, "contiguous nucleobases" means nucleobases immediately adjacent to each other in a nucleic acid.

As used herein, "percent identity" means the number of nucleobases in first nucleic acid that are identical to nucleobases at corresponding positions in a second nucleic acid, divided by the total number of nucleobases in the first nucleic acid. Percent identity (or percent complementarity) between particular stretches of nucleotide sequences within nucleic acid molecules or amino acid sequences within polypeptides can be determined routinely using BLAST programs (basic local alignment search tools) and Power-BLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). Herein, if reference is made to percent sequence identity, the higher percentages of sequence identity are preferred over the lower ones.

As used herein, "substantially identical" used herein may mean that a first and second nucleobase sequence are at least 60%, at least 65%, at least 70%, at least 75%, at least 80%, at least 85%, at least 90%, at least 95%, at least 97%, at least 98% at least 99%, or 100%, identical over a region of 8, 9, 10, 11, 12, 13, 14, 15, 16, 17, 18, 19, 20, 21, 22, 23, 24, 25, 30, 35, or 40 or more nucleobases.

As used herein, "hybridize" means the annealing of complementary nucleic acids that occurs through nucleobase complementarity.

As used herein, "mismatch" means a nucleobase of a first nucleic acid that is not capable of pairing with a nucleobase at a corresponding position of a second nucleic acid.

As used herein, "identical" means having the same nucleobase sequence.

As used herein, "hsa-miR-6883-5p" means the modified oligonucleotide having the nucleobase sequence set forth in SEQ ID NO: 1.

As used herein, "hsa-miR-149-3p" means the modified oligonucleotide having the nucleobase sequence set forth in SEQ ID NO: 2.

As used herein, "hsa-miR-6785-5p" means the modified oligonucleotide having the nucleobase sequence set forth in SEQ ID NO: 3.

As used herein, "hsa-miR-4728-5p" means the modified oligonucleotide having the nucleobase sequence set forth in SEQ ID NO: 4.

As used herein, "miRNA" or "miR" means a non-coding RNA from about 18 to about nucleobases in length.

As used herein, "oligomeric compound" means a compound comprising a polymer of linked monomeric subunits.

As used herein, "oligonucleotide" means a polymer of linked nucleosides, each of which can be modified or unmodified, independent from one another.

As used herein, "naturally occurring internucleoside linkage" means a 3' to 5' phosphodiester linkage between nucleosides.

As used herein, "natural sugar" means a sugar found in DNA (2'-H) or RNA (2'-OH).

As used herein, "natural nucleobase" means a nucleobase that is unmodified relative to its naturally occurring "internucleoside linkage" means a covalent linkage between adjacent nucleosides.

As used herein, "linked nucleosides" means nucleosides joined by a covalent linkage.

As used herein, "nucleobase" means a heterocyclic moiety capable of non-covalently pairing with another nucleobase.

As used herein, "nucleoside" means a nucleobase linked to a sugar.

As used herein, "nucleotide" means a nucleoside having a phosphate group covalently linked to the sugar portion of a nucleoside.

As used herein, "modified oligonucleotide" means an oligonucleotide having one or more modifications relative to a naturally occurring terminus, sugar, nucleobase, and/or internucleoside linkage.

As used herein, "modified internucleoside linkage" means any change from a naturally occurring internucleoside linkage.

As used herein, "phosphorothioate internucleoside linkage" means a linkage between nucleosides where one of the non-bridging atoms is a sulfur atom.

As used herein, "modified sugar" means substitution and/or any change from a natural sugar.

As used herein, "modified nucleobase" means any substitution and/or change from a natural nucleobase.

As used herein, "5-methylcytosine" means a cytosine modified with a methyl group attached to the 5' position.

As used herein, "2'-O-methyl sugar" or "2'-0-Me sugar" means a sugar having an O-methyl modification at the 2' position.

As used herein, "2'-O-methoxyethyl sugar" or "2'-MOE sugar" means a sugar having a O-methoxyethyl modification at the 2' position.

As used herein, "2'-0-fluoro" or "2'-F" means a sugar having a fluoro modification of the 2' position.

As used herein, "bicyclic sugar moiety" means a sugar modified by the bridging of two non-geminal ring atoms.

As used herein, "2'-O-methoxyethyl nucleoside" means a 2'-modified nucleoside having a 2'-O-methoxyethyl sugar modification.

As used herein, "2'-fluoro nucleoside" means a 2'-modified nucleoside having a 2'-fluoro sugar modification.

As used herein, "2'-O-methyl" nucleoside means a 2'-modified nucleoside having a 2'-O-methyl sugar modification.

As used herein, "bicyclic nucleoside" means a 2'-modified nucleoside having a bicyclic sugar moiety.

As used herein, "motif" means a pattern of modified and/or unmodified nucleobases, sugars, and/or internucleoside linkages in an oligonucleotide.

As used herein, a "fully modified oligonucleotide" means each nucleobase, each sugar, and/or each internucleoside linkage is modified.

As used herein, a "uniformly modified oligonucleotide" means each nucleobase, each sugar, and/or each internucleoside linkage has the same modification throughout the modified oligonucleotide.

As used herein, a "stabilizing modification" means a modification to a nucleoside that provides enhanced stability to a modified oligonucleotide, in the presence of nucleases, relative to that provided by 2'-deoxynucleosides linked by phosphodiester internucleoside linkages. For example, in some embodiments, a stabilizing modification is a stabilizing nucleoside modification. In some embodiments, a stabilizing modification is a internucleoside linkage modification.

As used herein, a "stabilizing nucleoside" means a nucleoside modified to provide enhanced nuclease stability to an oligonucleotide, relative to that provided by a 2'-deoxynucleoside. In one embodiment, a stabilizing nucleoside is a 2'-modified nucleoside.

As used herein, a "stabilizing internucleoside linkage" means an internucleoside linkage that provides enhanced nuclease stability to an oligonucleotide relative to that provided by a phosphodiester internucleoside linkage. In one embodiment, a stabilizing internucleoside linkage is a phosphorothioate internucleoside linkage.

The present disclosure provides oligonucleotides, such as modified oligonucleotides, consisting of 15 to 40 linked nucleobases, or a salt thereof, wherein the oligonucleotide comprises a nucleobase sequence that is at least 80% identical to a nucleobase sequence of hsa-miR-6883-5p, hsa-miR-149-3p, hsa-miR-6785-5p, or hsa-miR-4728-5p. In some embodiments, hsa-miR-6883-5p comprises the nucleobase sequence agggagggugugguauggaugu (SEQ ID NO: 1). In some embodiments, hsa-miR-149-3p comprises the nucleobase sequence agggagggacggggcugugc (SEQ ID NO: 2). In some embodiments, hsa-miR-6785-5p comprises the nucleobase sequence ugggagggcguggaugauggug (SEQ ID NO: 3). In some embodiments, hsa-miR-4728-5p comprises the nucleobase sequence ugggaggggagaggcagcaagca (SEQ ID NO: 4). In some embodiments, the oligonucleotide comprises a nucleobase sequence that is at least 85% identical to a nucleobase sequence of hsa-miR-6883-5p, hsa-miR-149-3p, hsa-miR-6785-5p, or hsa-miR-4728-5p. In some embodiments, the oligonucleotide comprises a nucleobase sequence that is at least 90% identical to a nucleobase sequence of hsa-miR-6883-5p, hsa-miR-149-3p, hsa-miR-6785-5p, or hsa-miR-4728-5p. In some embodiments, the oligonucleotide comprises a nucleobase sequence that is at least 95% identical to a nucleobase sequence of hsa-miR-6883-5p, hsa-miR-149-3p, hsa-miR-6785-5p, or hsa-miR-4728-5p.

In some embodiments, an oligonucleotide consists of 15 to 30 linked nucleobases. In some embodiments, an oligonucleotide consists of 19 to 24 linked nucleobases. In some embodiments, an oligonucleotide consists of 21 to 24 linked nucleobases. In some embodiments, the oligonucleotide consists of 15, 16, 17, 18, 19, 20, 21, 22, 23, 24, 25, 26, 27, 28, 29, 30, 31, 32, 33, 34, 35, 36, 37, 38, 39, or 40 linked nucleobases. In some embodiments, the oligonucleotide consists of 15, 16, 17, 18, 19, 20, 21, 22, 23, 24, 25, 26, 27, 28, 29, or 30 linked nucleobases. In some embodiments, the oligonucleotide consists of 15, 16, 17, 18, 19, 20, 21, 22, 23, 24, or 25 linked nucleobases. In some embodiments, the oligonucleotide comprises a nucleobase sequence comprising at least 16, at least 17, at least 18, at least 19, at least 20, at least 21, at least 22, or at least 23 contiguous nucleobases of a nucleobase sequence of SEQ ID NO: 1, SEQ ID NO: 2, SEQ ID NO: 3, or SEQ ID NO: 4. In each of these embodiments, the oligonucleotide can be a modified oligonucleotide.

In some embodiments, the nucleobase sequence of the oligonucleotide has no more than two mismatches compared to a nucleobase sequence selected from SEQ ID NO: 1, SEQ ID NO: 2, SEQ ID NO: 3, and SEQ ID NO: 4. In some embodiments, the nucleobase sequence of the oligonucleotide has no more than one mismatch compared to a nucleobase sequence selected from SEQ ID NO: 1, SEQ ID NO: 2, SEQ ID NO: 3, and SEQ ID NO: 4. In some embodiments, the nucleobase sequence of the oligonucleotide has one mismatch compared to a nucleobase sequence selected from SEQ ID NO: 1, SEQ ID NO: 2, SEQ ID NO: 3, and SEQ ID NO: 4. In some embodiments, the nucleobase sequence of the oligonucleotide has no mismatches compared to a nucleobase sequence selected from SEQ ID NO: 1, SEQ ID NO: 2, SEQ ID NO: 3, and SEQ ID NO: 4. In each of these embodiments, the oligonucleotide can be a modified oligonucleotide.

Suitable nucleic acids include, but are not limited to, deoxyribonucleic acid (DNA), ribonucleic acid (RNA), modified DNA or RNA, peptide nucleic acid (PNA), morpholino, locked nucleic acid (LNA), glycol nucleic acid (GNA), threose nucleic acid (TNA), DNA containing phosphorothioate residues (S-oligos) and derivatives thereof, or any combination thereof.

In some embodiments, one or more additional nucleobases may be added to either or both of the 3' terminus and 5' terminus of an oligonucleotide in comparison to the nucleobases sequences set forth in SEQ ID NO: 1, SEQ ID NO: 2, SEQ ID NO: 3, and SEQ ID NO: 4. In some embodiments, the one or more additional linked nucleobases are at the 3' terminus. In some embodiments, the one or more additional linked nucleosides are at the 5' terminus. In some embodiments, two additional linked nucleosides are linked to a terminus. In some embodiments, one additional nucleoside is linked to a terminus. In each of these embodiments, the oligonucleotide can be a modified oligonucleotide.

In some embodiments, the oligonucleotide comprises one or more modified internucleoside linkages, modified sugars, or modified nucleobases, or any combination thereof. The nucleobase sequences set forth herein, including but not limited to those found in the Examples and in the sequence listing, are independent of any modification to the nucleic acid. As such, nucleic acids defined by a SEQ ID NO: may comprise, independently, one or more modifications to one or more sugar moieties, to one or more internucleoside linkages, and/or to one or more nucleobases. A modified nucleobase, sugar, and/or internucleoside linkage may be selected over an unmodified form because of desirable properties such as, for example, enhanced cellular uptake, enhanced affinity for other oligonucleotides or nucleic acid targets and increased stability in the presence of nucleases.

In some embodiments, at least one internucleoside linkage is a modified internucleoside linkage. In some embodiments, each internucleoside linkage is a modified internucleoside linkage. In some embodiments, a modified internucleoside linkage comprises a phosphorus atom. In some embodiments, a modified oligonucleotide comprises at least one phosphorothioate internucleoside linkage. In some embodiments, each internucleoside linkage of a modified oligonucleotide is a phosphorothioate internucleoside linkage. In some embodiments, a modified internucleoside linkage does not comprise a phosphorus atom. In some such embodiments, an internucleoside linkage is formed by a short chain alkyl internucleoside linkage. In some such embodiments, an internucleoside linkage is formed by a cycloalkyl internucleoside linkages. In some such embodiments, an internucleoside linkage is formed by a mixed heteroatom and alkyl internucleoside linkage. In some such embodiments, an internucleoside linkage is formed by a mixed heteroatom and cycloalkyl internucleoside linkages. In some such embodiments, an internucleoside linkage is formed by one or more short chain heteroatomic internucleoside linkages. In some such embodiments, an internucleoside linkage is formed by one or more heterocyclic internucleoside linkages. In some such embodiments, an internucleoside linkage has an amide backbone. In some such embodiments, an internucleoside linkage has mixed N, O, S and $CH_2$ component parts.

In some embodiments, at least one nucleobase of the modified oligonucleotide comprises a modified sugar. In some embodiments, each of a plurality of nucleosides comprises a modified sugar. In some embodiments, each nucleoside of the modified oligonucleotide comprises a modified sugar. In each of these embodiments, the modified sugar may be a 2'-O-methoxyethyl sugar, a 2'-fluoro sugar, a 2'-O-methyl sugar, or a bicyclic sugar moiety. In some embodiments, each of a plurality of nucleosides comprises a 2'-O-methoxyethyl sugar and each of a plurality of nucleosides comprises a 2'-fluoro sugar.

In some embodiments, the sugar-modified nucleosides can further comprise a natural or modified heterocyclic base moiety and/or a natural or modified internucleoside linkage and may include further modifications independent from the sugar modification. In some embodiments, a sugar modified nucleoside is a 2'-modified nucleoside, wherein the sugar ring is modified at the 2' carbon from natural ribose or 2'-deoxyribose.

In some embodiments, a 2'-modified nucleoside has a bicyclic sugar moiety. In some such embodiments, the bicyclic sugar moiety is a D sugar in the alpha configuration. In some such embodiments, the bicyclic sugar moiety is a D sugar in the beta configuration. In some such embodiments, the bicyclic sugar moiety is an L sugar in the alpha configuration. In some such embodiments, the bicyclic sugar moiety is an L sugar in the beta configuration. In some embodiments, the bicyclic sugar moiety comprises a bridge group between the 2' and the 4'-carbon atoms. In some such embodiments, the bridge group comprises from 1 to 8 linked biradical groups. In some embodiments, the bicyclic sugar moiety comprises from 1 to 4 linked biradical groups. In some embodiments, the bicyclic sugar moiety comprises 2 or 3 linked biradical groups. In some embodiments, the bicyclic sugar moiety comprises 2 linked biradical groups. Biradical groups are well known in the art.

In some embodiments, the modified oligonucleotide comprises at least one modified nucleobase. In some embodiments, the modified nucleobase is selected from 5-hydroxymethyl cytosine, 7-deazaguanine and 7-deazaadenine. In some embodiments, the modified nucleobase is selected from 7-deaza-adenine, 7-deazaguanosine, 2-aminopyridine and 2-pyridone. In some embodiments, the modified nucleobase is selected from 5-substituted pyrimidines, 6-azapyrimidines and N-2, N-6 and 0-6 substituted purines, including 2 aminopropyladenine, 5-propynyluracil and 5-propynylcytosine. In some embodiments, the modified nucleobase is a 5-methylcytosine. In some embodiments, at least one nucleoside comprises a cytosine, wherein the cytosine is a 5-methylcytosine. In some embodiments, each cytosine is a 5-methylcytosine.

In some embodiments, a 2'-modified nucleoside comprises a 2'-substituent group selected from halo, allyl, amino, azido, —SH, —CN, —OCN, —$CF_3$, —$OCF_3$, —O—, —S—, or —N($R_m$)-alkyl; —O—, —S—, or —N($R_m$)-alkenyl; —O—, —S— or —N($R_m$)-alkynyl; —O-alkyleny-O-alkyl, alkynyl, alkaryl, aralkyl, —O-alkaryl, —O-aralkyl, —O($CH_2$)$_2SCH_3$, —O—($CH_2$)$_2$—O—N($R_m$)($R_n$) or —O—$CH_2$—C(=O)—N($R_m$)($R_n$), where each $R_m$ and $R_n$ is, independently, H, an amino protecting group or substituted or unsubstituted $C_{1-10}$alkyl. These 2'-substituent groups can be further substituted with one or more substituent groups independently selected from hydroxyl, amino, alkoxy, carboxy, benzyl, phenyl, nitro, thiol, thioalkoxy, halogen, alkyl, aryl, alkenyl and alkynyl.

In some embodiments, a 2'-modified nucleoside comprises a 2'-substituent group selected from F, $NH_2$, $N_3$, $OCF_3$, O—$CH_3$, O($CH_2$)$_3NH_2$, $CH_2$—CH=$CH_2$, O—$CH_2$—CH=$CH_2$, $OCH_2CH_2OCH_3$, O($CH_2$)$_2SCH_3$, O—($CH_2$)$_2$—O—N($R_m$)($R_n$), —O($CH_2$)$_2$O($CH_2$)$_2$N($CH_3$)$_2$, and N-substituted acetamide (O—$CH_2$—C(=O)—N(Rm)($R_n$) where each $R_m$ and $R_n$ is, independently, H, an amino protecting group or substituted or unsubstituted $C_{1-10}$alkyl. In some embodiments, a 2'-modified nucleoside comprises a 2'-substituent group selected from F, $OCF_3$, O—$CH_3$, $OCH_2CH_2OCH_3$, 2'-O($CH_2$)$_2SCH_3$, O—($CH_2$)$_2$—O—N($CH_3$)$_2$, —O($CH_2$)$_2$O($CH_2$)$_2$N($CH_3$)$_2$, and O—$CH_2$—C(=O)—N(H)$CH_3$.

In some embodiments, a 2'-modified nucleoside comprises a 2'-substituent group selected from F, O—$CH_3$, and $OCH_2CH_2OCH_3$. In some embodiments, a sugar-modified nucleoside is a 4'-thio modified nucleoside. In some embodiments, a sugar-modified nucleoside is a 4'-thio-2'-modified nucleoside. A 4'-thio modified nucleoside has a B-D-ribonucleoside where the 4'-O replaced with 4'-S. A 4'-thio-2'-modified nucleoside is a 4'-thio modified nucleoside having the 2'-OH replaced with a 2'-substituent group. Suitable 2'-substituent groups include 2'-$OCH_3$, 2-O—($CH_2$)$_2$—$OCH_3$, and 2'-F.

In some embodiments, a modified nucleobase comprises a polycyclic heterocycle. In some embodiments, a modified nucleobase comprises a tricyclic heterocycle. In some embodiments, a modified nucleobase comprises a phenoxazine derivative. In some embodiments, the phenoxazine can be further modified to form a nucleobase known in the art as a G-clamp.

In some embodiments, the oligonucleotide compound comprises a modified oligonucleotide conjugated to one or more moieties which enhance the activity, cellular distribution or cellular uptake of the resulting antisense oligonucleotides. In some such embodiments, the moiety is a cholesterol moiety or a lipid moiety. Additional moieties for conjugation include carbohydrates, phospholipids, biotin, phenazine, folate, phenanthridine, anthraquinone, acridine, fluoresceins, rhodamines, coumarins, and dyes. In some embodiments, a conjugate group is attached directly to a modified oligonucleotide. In some embodiments, a conjugate group is attached to a modified oligonucleotide by a linking moiety selected from amino, hydroxyl, carboxylic acid, thiol, unsaturations (e.g., double or triple bonds), 8-amino-3,6-dioxaoctanoic acid (ADO), succinimidyl4-(N-maleimidomethyl)cyclohexane-1-carboxylate (SMCC), 6-aminohexanoic acid (AHEX or AHA), substituted $C_{1-10}$alkyl, substituted or unsubstituted $C_{2-10}$alkenyl, and substituted or unsubstituted $C_{2-10}$alkynyl. In some such embodiments, a substituent group is selected from hydroxyl, amino, alkoxy, carboxy, benzyl, phenyl, nitro, thiol, thioalkoxy, halogen, alkyl, aryl, alkenyl and alkynyl.

In some such embodiments, the oligonucleotide compound comprises a modified oligonucleotide having one or more stabilizing groups that are attached to one or both termini of a modified oligonucleotide to enhance properties such as, for example, nuclease stability. Included in stabilizing groups are cap structures. These terminal modifications protect a modified oligonucleotide from exonuclease degradation, and can help in delivery and/or localization within a cell. The cap can be present at the 5'-terminus (5'-cap), or at the 3'-terminus (3'-cap), or can be present on both termini Cap structures include, for example, inverted deoxy abasic caps.

Additional cap structures include, but are not limited to, a 4',5'-methylene nucleotide, a 1-(beta-D-erythrofuranosyl) nucleotide, a 4'-thio nucleotide, a carbocyclic nucleotide, a 1,5-anhydrohexitol nucleotide, an L-nucleotide, an alpha-nucleotide, a modified base nucleotide, a phosphorodithioate linkage, a threopentofuranosyl nucleotide, an acyclic 3',4'-seco nucleotide, an acyclic 3,4-dihydroxybutyl nucleotide, an acyclic 3,5-dihydroxypentyl nucleotide, a 3'-3'-inverted nucleotide moiety, a 3'-3'-inverted abasic moiety, a 3'-2'-inverted nucleotide moiety, a 3'-2'-inverted abasic moiety, a 1,4-butanediol phosphate, a 3'-phosphoramidate, a hexylphosphate, an aminohexyl phosphate, a 3'-phosphate, a 3'-phosphorothioate, a phosphorodithioate, a bridging methylphosphonate moiety, and a non-bridging methylphosphonate moiety 5'-amino-alkyl phosphate, a 1,3-diamino-2-propyl phosphate, 3-aminopropyl phosphate, a 6-aminohexyl phosphate, a 1,2-aminododecyl phosphate, a hydroxypropyl phosphate, a 5'-5'-inverted nucleotide moiety, a 5'-5'-inverted abasic moiety, a 5'-phosphoramidate, a 5'-phosphorothioate, a 5'-amino, a bridging and/or non-bridging 5'-phosphoramidate, a phosphorothioate, and a 5'-mercapto moiety.

The present disclosure also provides pharmaceutical compositions comprising one or more of the oligonucleotides described herein. In some embodiments, the oligonucleotide consists of 15 to 30 linked nucleosides, or a salt thereof, wherein the modified oligonucleotide comprises a nucleobase sequence that is at least 80% identical to a nucleobase sequence selected from SEQ ID NO: 1, SEQ ID NO: 2, SEQ ID NO: 3, SEQ ID NO: 4, and a pharmaceutically acceptable carrier or diluent. In each of these embodiments, the oligonucleotide can be a modified oligonucleotide.

In some embodiments, the compositions may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions, such as dyes, flavoring agents, preservatives, antioxidants, opacifiers, thickening agents and stabilizers. However, such materials, when added, should not unduly interfere with the biological activities of the components of the compositions. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the oligonucleotide(s) of the formulation.

In some embodiments, pharmaceutical compositions comprise one or more modified oligonucleotides and one or more excipients. In some such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In some embodiments, a pharmaceutical composition is prepared using known techniques, including, but not limited to mixing, dissolving, granulating, dragee-making, levigating, emulsifying, encapsulating, entrapping or tab letting processes.

In some embodiments, a pharmaceutical composition is a liquid (e.g., a suspension, elixir and/or solution). In some such embodiments, a liquid pharmaceutical composition is prepared using ingredients known in the art, including, but not limited to, water, glycols, oils, alcohols, flavoring agents, preservatives, and coloring agents.

In some embodiments, a pharmaceutical composition is a solid (e.g., a powder, tablet, and/or capsule). In some such embodiments, a solid pharmaceutical composition comprising one or more oligonucleotides is prepared using ingredients known in the art, including, but not limited to, starches, sugars, diluents, granulating agents, lubricants, binders, and disintegrating agents.

In some embodiments, a pharmaceutical composition is formulated as a depot preparation. Some such depot preparations are typically longer acting than non-depot preparations. In some embodiments, such preparations are administered by implantation (for example subcutaneously or intramuscularly) or by intramuscular injection. In some embodiments, depot preparations are prepared using suitable polymeric or hydrophobic materials (for example an emulsion in an acceptable oil) or ion exchange resins, or as sparingly soluble derivatives, for example, as a sparingly soluble salt.

In some embodiments, a pharmaceutical composition comprises a delivery system. Examples of delivery systems include, but are not limited to, liposomes and emulsions. Delivery systems are useful for preparing pharmaceutical compositions including those comprising hydrophobic compounds. In some embodiments, some organic solvents such as dimethylsulfoxide are used. In some embodiments, presently available RNAi packaging technology can be used to packing the miRNA in lipid complexes and to deliver the miRNA. The delivery system can also comprise nanoparticules or nano-complexes. The delivery system can also comprise bacterial mini-cells comprising RNA duplexes.

In some embodiments, a pharmaceutical composition comprises one or more tissue-specific delivery molecules designed to deliver the one or more pharmaceutical agents to specific tissues or cell types. For example, in some embodiments, pharmaceutical compositions include liposomes coated with a tissue-specific antibody.

In some embodiments, a pharmaceutical composition comprises a cosolvent system. Some such co-solvent systems comprise, for example, benzyl alcohol, a nonpolar surfactant, a water-miscible organic polymer, and an aqueous phase. In some embodiments, such cosolvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In some embodiments, a pharmaceutical composition comprises a sustained-release system. A non-limiting example of such a sustained-release system is a semipermeable matrix of solid hydrophobic polymers. In some embodiments, sustained-release systems may, depending on their chemical nature, release pharmaceutical agents over a period of hours, days, weeks or months.

In some embodiments, a pharmaceutical composition is prepared for oral administration. In some such embodiments, a pharmaceutical composition is formulated by combining one or more compounds comprising any one or more of the oligonucleotides described herein with one or more pharmaceutically acceptable carriers. Some such carriers enable pharmaceutical compositions to be formulated as tablets, pills, dragees, capsules, liquids, gels, syrups, slurries, suspensions and the like, for oral ingestion by a subject. In some embodiments, pharmaceutical compositions for oral use are obtained by mixing oligonucleotide and one or more solid excipient. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In some embodiments, such a mixture is optionally ground and auxiliaries are optionally added. In some embodiments, pharmaceutical compositions are formed to obtain tablets or dragee cores. In some embodiments, disintegrating agents (e.g., cross-linked polyvinylpyrrolidone, agar, or alginic acid or a salt thereof, such as sodium alginate) are added.

In some embodiments, dragee cores are provided with coatings. In some such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In some embodiments, pharmaceutical compositions for oral administration are push-fit capsules made of gelatin. Some such push-fit capsules comprise one or more of the oligonucleotides described herein in admixture with one or more filler such as lactose, binders such as starches, and/or lubricants such as talc or magnesium stearate and, optionally, stabilizers. In some embodiments, pharmaceutical compositions for oral administration are soft, sealed capsules made of gelatin and a plasticizer, such as glycerol or sorbitol. In some soft capsules, one or more of the oligonucleotides described herein are be dissolved or suspended in suitable liquids, such as fatty oils, liquid paraffin, or liquid polyethylene glycols. In addition, stabilizers may be added.

In some embodiments, pharmaceutical compositions are prepared for buccal administration. Some such pharmaceutical compositions are tablets or lozenges formulated in conventional manner.

In some embodiments, a pharmaceutical composition is prepared for administration by injection (e.g., intravenous, intraperitoneal, subcutaneous, intramuscular, etc.). In some such embodiments, a pharmaceutical composition comprises a carrier and is formulated in aqueous solution, such as water or physiologically compatible buffers such as Hanks's solution, Ringer's solution, or physiological saline buffer. In some embodiments, other ingredients are included (e.g., ingredients that aid in solubility or serve as preservatives). In some embodiments, injectable suspensions are prepared using appropriate liquid carriers, suspending agents and the like. Some pharmaceutical compositions for injection are presented in unit dosage form, e.g., in ampoules or in multi-dose containers. Some pharmaceutical compositions for injection are suspensions, solutions or emulsions in oily or aqueous vehicles, and may contain formulatory agents such as suspending, stabilizing and/or dispersing agents. Some solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the oligonucleotides described herein to allow for the preparation of highly concentrated solutions. In some embodiments, a pharmaceutical composition is prepared for transmucosal administration. In some such embodiments penetrants appropriate to the barrier to be permeated are used in the formulation. Such penetrants are generally known in the art.

In some embodiments, a pharmaceutical composition is prepared for administration by inhalation. Some such pharmaceutical compositions for inhalation are prepared in the form of an aerosol spray in a pressurized pack or a nebulizer. Some such pharmaceutical compositions comprise a propellant, e.g., dichlorodifluoromethane, trichlorofluoromethane, dichlorotetrafluoroethane, carbon dioxide or other suitable gas. In some embodiments using a pressurized aerosol, the dosage unit may be determined with a valve that delivers a metered amount. In some embodiments, capsules and cartridges for use in an inhaler or insufflator may be formulated. Some such formulations comprise a powder mixture of one or more of the oligonucleotides described herein and a suitable powder base such as lactose or starch.

In some embodiments, a pharmaceutical composition is prepared for rectal administration, such as a suppositories or retention enema. Some such pharmaceutical compositions comprise known ingredients, such as cocoa butter and/or other glycerides.

In some embodiments, a pharmaceutical composition is prepared for topical administration. Some such pharmaceutical compositions comprise bland moisturizing bases, such as ointments or creams. Exemplary suitable ointment bases include, but are not limited to, petrolatum, petrolatum plus volatile silicones, and lanolin and water in oil emulsions. Exemplary suitable cream bases include, but are not limited to, cold cream and hydrophilic ointment.

In some embodiments, a pharmaceutical composition comprises a modified oligonucleotide in a therapeutically effective amount. In some embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In some embodiments, the pharmaceutical composition may further comprise at least one additional therapeutic agent. The additional therapeutic agent may be a chemotherapeutic agent. In some embodiments, the chemotherapeutic agent is a platinum-based chemotherapeutic agent such as, for example, cisplatin, carboplatin, oxaliplatin, nedaplatin, triplatin tetranitrate, phenanthriplatin, picoplatin, or satraplatin. In some embodiments, the chemotherapeutic agent is a taxane such as, for example, paclitaxel, docetaxel, or cabazitaxel. In some embodiments, the chemotherapeutic agent is a type I topoisomerase inhibitor such as, for example, irinotecan, topotecan, camptothecin, or lamellarin D. In some embodiments, the chemotherapeutic agent is a type II topoisomerase inhibitor such as, for example, etoposide (VP-16), teniposide, doxorubicin, daunorubicin, mitoxantrone, amsacrine, ellipticines, aurintricarboxylic acid, or HU-331. In some embodiments, the chemotherapeutic agent is a combination of chemotherapeutic agents such as, for example, CHOP (cyclophosphamide, doxorubicin (hydroxydaunomycin), vincristine (Oncovie®), and prednisolone). In some embodiments, the chemotherapeutic agent may be selected from 5-fluorouracil, cisplatin, gemcitabine, doxorubicine, mitomycin c, sorafenib, etoposide, carboplatin, epirubicin, irinotecan and oxaliplatin. In some embodiments, the chemotherapeutic is 5-fluorouracil or irinotecan. The pharmaceutical composition may comprise one or more of the oligonucleotide compounds described herein in combination with one or more of the additional therapeutic agents. For example, the pharmaceutical composition may comprise an one of more oligonucleotides consisting of 15 to 40 linked nucleobases, or a salt thereof, wherein the oligonucleotide comprises a nucleobase sequence that is at least 80% identical to a nucleobase sequence of hsa-miR-6883-5p, hsa-miR-149-3p, hsa-miR-6785-5p, or hsa-miR-4728-5p, in combination with any one or more of 5-fluorouracil, cisplatin, gemcitabine, doxorubicine, mitomycin c, sorafenib, etoposide, carboplatin, epirubicin, irinotecan and oxaliplatin. In some embodiments, the pharmaceutical composition comprises an one of more oligonucleotides consisting of 15 to 40 linked nucleobases, or a salt thereof, wherein the oligonucleotide comprises a nucleobase sequence that is at least 80% identical to a nucleobase sequence of hsa-miR-6883-5p, hsa-miR-149-3p, hsa-miR-6785-5p, or hsa-miR-4728-5p, in combination with 5-fluorouracil and/or irinotecan.

In some embodiments, an additional therapy may be a pharmaceutical agent that enhances the body's immune system, including low-dose cyclophosphamide, thymostimulin, vitamins and nutritional supplements (e.g., antioxidants, including vitamins A, C, E, beta-carotene, zinc, selenium, glutathione, coenzyme Q-10 and echinacea), and vaccines, e.g., the immunostimulating complex (ISCOM), which comprises a vaccine formulation that combines a multimeric presentation of antigen and an adjuvant.

In some embodiments, a pharmaceutical agent that induces the expression of the miRNAs disclosed herein, or induces the expression of PER1 or regulates the expression of PER1, such as atypical psychotics including, but not limited to, quetiapine and haloperidol can be used. In some embodiments, the pharmaceutical agent is melatonin. In some embodiments, the pharmaceutical agent for inducing the expression of the miRNAs or PER1 is forskolin, interleukin-6, or Sp-5,6-DCI-cBiMPS. These pharmaceutical agents may be present in a pharmaceutical composition.

The present disclosure also provides methods for treating a tumor or cancer, comprising administering to a subject in need thereof one or more of the oligonucleotides described herein, and/or a pharmaceutical agent that induces the production of the one or more oligonucleotides and/or induces PER1 expression. In some embodiments, the oligonucleotide consists of 15 to 30 linked nucleosides, wherein the oligonucleotide comprises a nucleobase sequence that is at least 80% identical to a nucleobase sequence selected from SEQ ID NO: 1, SEQ ID NO: 2, SEQ ID NO: 3, and SEQ ID NO: 4. In some embodiments, the oligonucleotide is a modified oligonucleotide as described herein.

The present disclosure also provides methods for treating a tumor or cancer, comprising administering to a subject in need thereof a pharmaceutical composition comprising one or more of the oligonucleotides described herein, or a pharmaceutical agent that induces the production of the one or more oligonucleotides and/or induces PER1 expression. In some embodiments, the oligonucleotide consists of 15 to 30 linked nucleosides, wherein the oligonucleotide comprises a nucleobase sequence that is at least 80% identical to a nucleobase sequence selected from SEQ ID NO: 1, SEQ ID NO: 2, SEQ ID NO: 3, and SEQ ID NO: 4. In some embodiments, the oligonucleotide is a modified oligonucleotide as described herein.

In some embodiments, the cancer being treated is a tumor or solid tumor. In some embodiments, the cancer cell or tumor overexpresses a CDK, such as CDK4 and/or CDK6. In some embodiments, the cancer cell or tumor exhibits a loss of p16. In some embodiments, the cancer cell or tumor exhibits a loss of Rb. In some embodiments, the cancer cell or tumor exhibits overexpression of cyclin D1. In some embodiments, the cancer cell or tumor is in need of inhibition of a CDK, such as CDK4 and/or CDK6. In some embodiments, the tumor or cancer is pancreatic, melanoma, colorectal, colon, lung, breast, or leukemia. In some embodiments, the cancer is colon cancer, colorectal cancer, lung cancer, or melanoma. In some embodiments, the cancer is colon cancer. In some embodiments, the cancer is pancreatic cancer. In some embodiments, the cancer is colorectal cancer. In some embodiments, the cancer is lung cancer. In some embodiments, the cancer is melanoma. In some embodiments, the tumors may be less well-oxygenated than the normal tissues from which they arose (i.e., "tumor hypoxia") which, in some cases, may lead to resistance to radiotherapy and anticancer chemotherapy as well as predisposing for increased tumor metastases.

In some embodiments, the methods described herein use one or more oligonucleotides or modified oligonucleotides that is/are targeted to CDK4 and/or CDK6. The oligonucleotides or modified oligonucleotides can be administered with or without being integrated into a vector. The oligonucleotides or modified oligonucleotides can also be used in the form of double stranded entities, whereby the appropriate strand is produced inside a cell.

In some embodiments, administration of a compound comprises intravenous administration, subcutaneous administration, intratumoral administration, intraperitoneal administration, or chemoembolization.

In some embodiments, the methods further comprise administering at least one additional therapy. The additional therapy may be a chemotherapeutic agent. The chemotherapeutic agent may be selected from 5-fluorouracil, cisplatin, gemcitabine, doxorubicine, mitomycin c, sorafenib, etoposide, carboplatin, epirubicin, irinotecan and oxaliplatin. In some embodiments, the chemotherapeutic is 5-fluorouracil or irinotecan. The additional therapy may be administered at the same time, less frequently, or more frequently than a compound or pharmaceutical composition described herein. In some embodiments, the additional therapy is surgical resection and/or chemoembolization.

In some embodiments, any one or more of the oligonucleotides described herein is administered at a dose selected from 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, and 800 mg. The oligonucleotide may be administered one per day, once per week, once per two weeks, once per three weeks, or once per four weeks.

In some embodiments, the administration of a compound results in reduction of tumor size and/or tumor number. In some embodiments, the administration of a compound prevents an increase in tumor size and/or tumor number. In some embodiments, the administration of a compound prevents, slows, and/or stops metastatic progression. In some embodiments, the administration of a compound extends the overall survival time of the subject. In some embodiments, the administration of a compound extends the progression-free survival of the subject. In some embodiments, administration of a compound prevents the recurrence of tumors. In some embodiments, administration of a compound prevents recurrence of tumor metastasis.

A subject may be diagnosed with a tumor or cancer, such as colon cancer, following the administration of medical tests well known to those in the medical profession. The diagnosis of a tumor or cancer, such as colon cancer, can be made by imaging tests such as ultrasound, helical computed tomography (CT) scan, triple phase CT scan, or magnetic resonance imaging (MRI). The imaging tests allow the assessment of the tumor size, number, location, metastasis, patency and/or invasion of adjacent tissue by the tumor. This assessment aids the decision as to the mode of therapeutic or palliative intervention that is appropriate. The final diagnosis is typically confirmed by needle biopsy and histopathological examination.

Administration of a pharmaceutical composition to a subject having a tumor can result in one or more clinically desirable outcomes. Such clinically desirable outcomes include reduction of tumor number or reduction of tumor size. Additional clinically desirable outcomes include the extension of overall survival time of the subject, and/or extension of progression-free survival time of the subject. In some embodiments, administration of a pharmaceutical composition prevents an increase in tumor size and/or tumor number. In some embodiments, administration of a pharmaceutical composition prevents metastatic progression. In some embodiments, administration of a pharmaceutical composition slows or stops metastatic progression. In some embodiments, administration of a pharmaceutical composition prevents the recurrence of tumors. In some embodiments, administration of a pharmaceutical composition prevents recurrence of tumor metastasis. In some embodiments, administration of a pharmaceutical composition prevents the recurrence of tumors. Administration of a pharmaceutical composition to tumor cells may result in desirable phenotypic effects. In some embodiments, an oligonucleotide may stop, slow or reduce the uncontrolled proliferation of tumor cells. In some embodiments, an oligonucleotide may induce apoptosis in tumor cells. In some embodiments, an oligonucleotide may reduce tumor cell survival.

In some embodiments, one or more pharmaceutical compositions and one or more other pharmaceutical agents are administered at the same time. In some embodiments, one or more pharmaceutical compositions and one or more other pharmaceutical agents are administered at different times. In some embodiments, one or more pharmaceutical compositions and one or more other pharmaceutical agents are prepared together in a single formulation. In some embodiments, one or more pharmaceutical compositions and one or more other pharmaceutical agents are prepared separately.

In some embodiments, a pharmaceutical composition is administered in the form of a dosage unit (e.g., tablet, capsule, bolus, etc.). In some embodiments, such pharmaceutical compositions comprise any one or more of the oligonucleotides or modified oligonucleotides described herein in a dose selected from 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 270 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, and 800 mg. In some such embodiments, a pharmaceutical composition comprises a dose of modified oligonucleotide selected from 25 mg, 50 mg, 75 mg, 100 mg, 150 mg, 200 mg, 250 mg, 300 mg, 350 mg, 400 mg, 500 mg, 600 mg, 700 mg, and 800 mg.

In some embodiments, a pharmaceutical agent is sterile lyophilized oligonucleotide that is reconstituted with a suitable diluent, e.g., sterile water for injection or sterile saline for injection. The reconstituted product is administered as a subcutaneous injection or as an intravenous infusion after dilution into saline. The lyophilized drug product consists of any one or more of the oligonucleotides or modified oligonucleotides described herein which has been prepared in water for injection, or in saline for injection, adjusted to pH 7.0-9.0 with acid or base during preparation, and then lyophilized. The lyophilized modified oligonucleotide may be 25-800 mg of any one or more of the oligonucleotides or modified oligonucleotides described herein. It is understood that this encompasses 25, 50, 75, 100, 125, 150, 175, 200, 225, 250, 275, 300, 325, 350, 375, 425, 450, 475, 500, 525, 550, 575, 600, 625, 650, 675, 700, 725, 750, 775, and 800 mg of modified lyophilized oligonucleotide. The lyophilized drug product may be packaged in a 2 mL Type I, clear glass vial (ammonium sulfate-treated), stoppered with a bromobutyl rubber closure and sealed with an aluminum FLIP-OFF® overseal.

The present disclosure also provides methods of detecting and/or determining the level of any one or more of the miRNA described herein. The detection and/or level determination can be carried out by conventional means known in the art. The level of particular miRNAs can be used as disease progress markers for any of the cancers disclosed herein. The miRNAs can also be used to predict and/or monitor a therapeutic response.

The present disclosure also provides any one or more of the oligonucleotide compounds described herein, or compositions comprising the same, for use in treating or preventing cancer or tumors.

The present disclosure also provides any one or more of the oligonucleotide compounds described herein, or compositions comprising the same, for use in the manufacture of a medicament for treating or preventing cancer or tumors.

The present disclosure also provides uses of any one or more of the oligonucleotide compounds described herein, or compositions comprising the same, for treating or preventing cancer or tumors.

The present disclosure also provides uses of any one or more of the oligonucleotide compounds described herein, or compositions comprising the same, in the manufacture of a medicament for treating or preventing cancer or tumors.

The present disclosure also provides any one or more of the oligonucleotide compounds described herein, or compositions comprising the same, or methods of preparing the same, or methods of using the same, or uses any one or more of the oligonucleotide compounds described herein, or compositions comprising the same, substantially as described with reference to the accompanying examples and/or figures.

In order that the subject matter disclosed herein may be more efficiently understood, examples are provided below. It should be understood that these examples are for illustrative purposes only and are not to be construed as limiting the claimed subject matter in any manner. Throughout these examples, molecular cloning reactions, and other standard recombinant DNA techniques, were carried out according to methods described in Maniatis et al., Molecular Cloning—A Laboratory Manual, 2nd ed., Cold Spring Harbor Press (1989), using commercially available reagents, except where otherwise noted.

EXAMPLES

Example 1: General Materials and Methods

Cell culture and reagents: All colorectal, pancreatic and melanoma cell lines were obtained from American Type Culture Collection and maintained in the recommended media. miRNA mimics for hsa-miR-6883-5p, hsa-miR-149*, and hsa-miR-206 (HMI2616, HMI0241 and HMI0364) were purchased from Sigma-Aldrich. siRNA for CDK4 and CDK6 (sc-29261 and sc-29264) were purchased from Santa Cruz Biotechnology. The CDK4-Luciferase construct was obtained from Origene Technologies.

Transfection of miRNA mimics, siRNA and plasmid constructs: All miRNA mimics and siRNA transfections were performed by reverse transfection using Lipofectamine RNAiMAX (Life technologies, Grand Island, N.Y.). 80 nM siRNA was used in all experiments for HT-29, RKO and SW-480 cell lines. 40 nM siRNA was used for HCT-116 cells. miRNA mimics were transfected at concentrations of either 25 nM, 50 nM, or 100 nM, as indicated in respective assays. CDK4-Luciferase vector was transfected in HCT-116 cells using Lipofectamine 3000 (Life technologies, Grand Island, N.Y.) and stable cells were selected using G418 antibiotic (500 μg/mL).

Luciferase assays: CDK4-Luciferase containing stable HCT-116 cells were reverse-transfected with either scramble duplex or 50 nM miRNA mimics Luciferase signal was detected 48 hours post-transfection and Relative Luciferase Units (RLU) were calculated by normalizing luciferase signal per μg of protein per assay well. All transfections were performed in triplicates and reported as RLU units±SEM.

Cell Proliferation assays: Five thousand to ten thousand cells were reverse transfected with either scramble duplex or miRNA to a net concentration of 50 nM and plated in 96-well plate. Cell viability was measured 72 hours post-transfection using CellTiter-Glo® Luminescent Cell Viability Assay (Promega). Percent cell viability was calculated by normalizing the luminescence signal to scramble duplex wells. All transfections were performed in triplicates and reported as % Viability±SEM.

Cell Cycle Analysis: All cell lines were reverse transfected with either scramble duplex or miRNA mimic. At 72 hours post-transfection, both floating and adherent cells were collected and fixed in 70% ethanol, followed by RNase A treatment and PI staining. Cell death (sub-G1) was quantified by propidium iodide (PI) staining and fluorescence-activated cell sorting (FACS). Flo-Jo analysis was performed to quantify the distribution of cells in G1, S, and G2-M phases of cell cycle under different transfection conditions.

Colony formation assays: A total of $0.1 \times 10^6$ cells were reverse transfected with either scramble duplex or miRNA mimics to net concentration of 50 nM (HT-29 and HCT-116) or 100 nM (RKO and SW-480) for 72 hours. At 72 hours, transfected cells were harvested and 500 cells per treatment group were plated in triplicate in 6-well plates for colony formation. Colonies were crystal violet stained on Day 14, imaged, counted and reported as the number of colonies±SEM.

Quantitative RT-PCR (qRT-PCR): Total RNA, which includes miRNA, was isolated using the Quick-RNA™ MiniPrep kit (Zymo Research, Irvine, Calif.). One μg of total RNA from each sample was subjected to cDNA synthesis using SuperScript® III Reverse Transcriptase kit (Life Technologies, Grand Island, N.Y.), for detection of CDK4, CDK6, and housekeeping genes. For detection of miRNAs, 0.5 μg of total RNA was reverse transcribed using TaqMan® MicroRNA Reverse Transcription Kit (Life Technologies, Grand Island, N.Y.). The relative expression of the reported genes and miRNAs was determined using real-time PCR performed on Applied Biosystems 7900HT Fast Real-Time PCR system. GAPDH and RNU6B were used as the endogenous controls for mRNA and miRNA samples respectively. Each cDNA sample was amplified using Power SYBR Green (Applied Biosystems, CA) and miRNA components were quantified using TaqMan® Universal Master Mix II, no UNG (Applied Biosystems, CA). TaqMan miRNA assays were purchased from Applied Biosystems and used as per manufacturer's instructions.

Western blot: Western blotting was performed by routine and well known procedures. The following antibodies were used: CDK4 (Santa Cruz Biotechnology, sc-260), CDK6 (CST, D4S8S), CDK1 (Santa Cruz Biotechnology, sc-54), Cyclin-D1 (CST, 92G2), p-Rb (S795) (CST, 9301S), Total Rb, BCLxL (CST, 2764S), PARP (CST, 9542), p53-DO1 (Santa Cruz Biotechnology, sc-126), p21 (Calbiochem, OP64), and β-actin (Sigma, A5441).

Statistical analysis: Data are presented as the mean±standard error of mean from at least three replicates. The Student's two-tailed t-test in GraphPad Prism was used for pairwise analysis. Statistically significant changes (*p≤0.05, p≤0.01 and *≤0.001) are indicated.

Example 2: CDK4 and CDK6 are Important Therapeutic Targets and can be Regulated with miRNAs in CRC Events of overexpression of cell cycle oncogenes (CDKs, Cyclins) and suppression of tumor suppressors (p16, Rb) in the CDK4/6-Rb pathway are mutually exclusive and tumor-type specific. To assess the status of these events in CRC, RNA-sequencing data from The Cancer Genome Atlas (TCGA) for normal and tumor samples (T/N) was analyzed. Of the 50 T/N samples analyzed as shown in FIG. 1A, both CDK4 (left panel) and CDK6 (right panel) expression were significantly high in the tumor samples (p=2.2 e-16 and p=1.594 e-08 respectively). There was no significant change in the RNA levels of tumor suppressors p16 and Rb. These findings are in consensus with previous reports which have shown overexpression of CDK4 and CDK6 in IHC samples with differences on staging (Zhao et al., World J. Gastroenterol., 2003, 9, 2202-2206; and Zhao et al., World J. Gastroenterol., 2006, 12, 6391-6396).

Figure 1C:
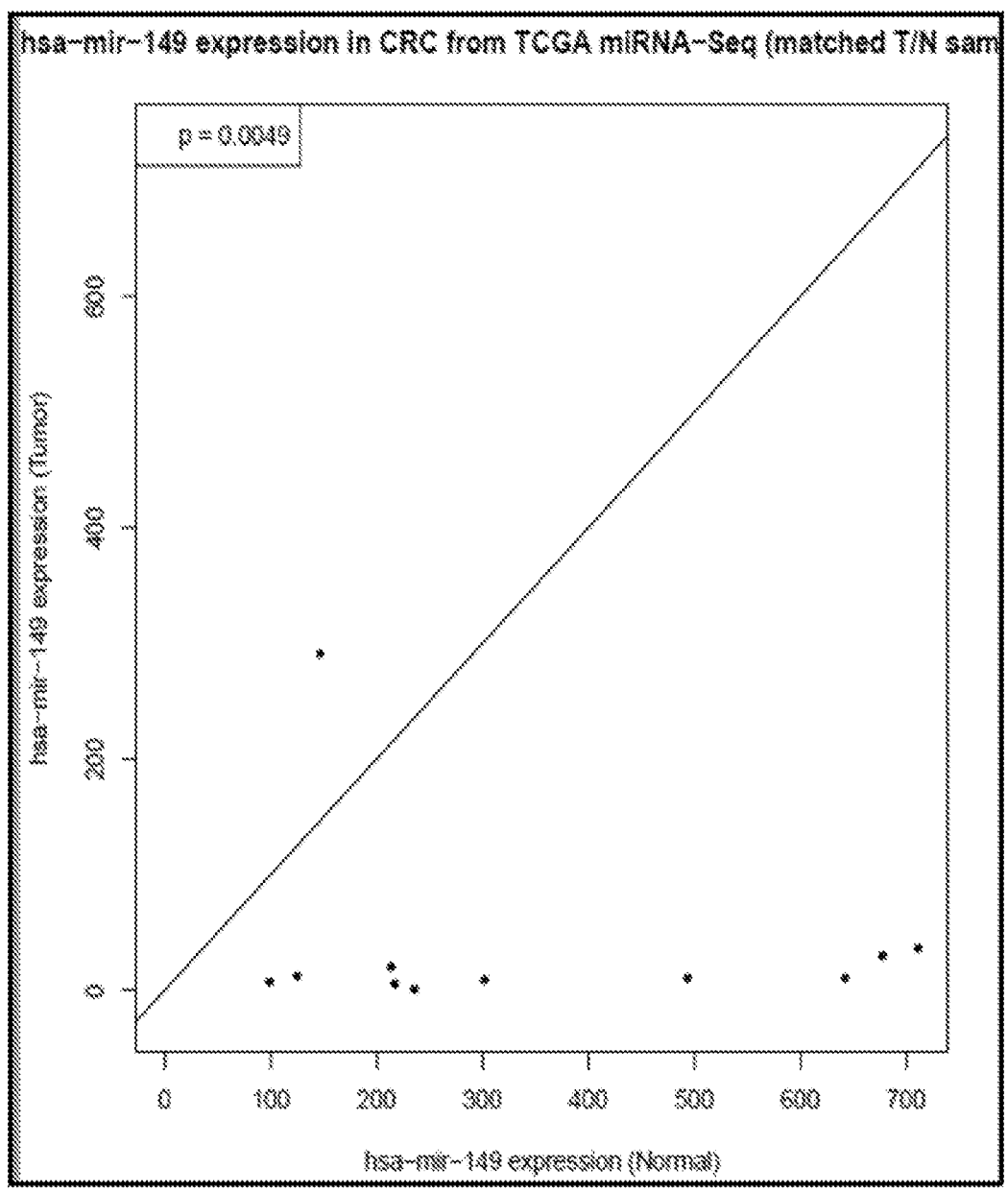
Figure 1C:
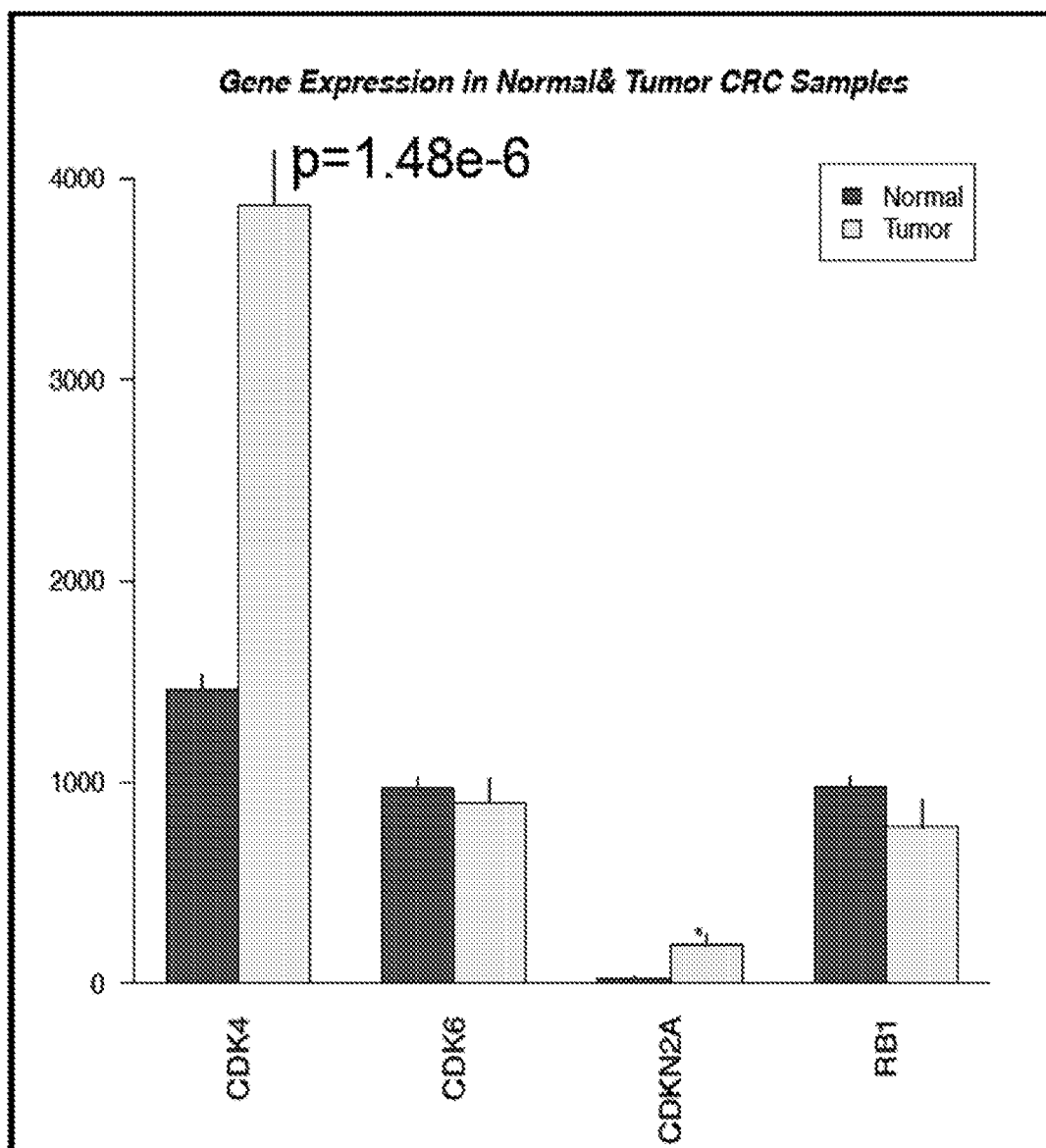

To determine whether CDK4 and CDK6 can be negatively regulated by miRNAs, an in silico approach using TargetScan, an online computational algorithm, was taken to find miRNAs that could target the 3'UTR of both CDK4 and CDK6. There have been prior reports of conserved miRNAs, including miR-206, miR-124-3p, and miR-15-5p, that examine CDK4 targeting alone in melanoma and other tumor types. One goal was to focus on novel and uncharacterized miRNAs that also had relevance in CRC and could target both CDK4 and CDK6. Based on a combination of TCGA analysis and TargetScan, a new family of miRNAs encompassing miRs 6883-5p, 149*, 6785-5p and 4728-5p was developed. Each of these miRNAs were predicted to target both CDK4 and CDK6 3'UTR with 8-mer and 7-mer-1A binding sites (Table 1 and 2, respectively, of FIG. 1B). miRs 6883-5p and 149* were further examined for their novelty and relevance to CRC. As seen in FIG. 1C, expression of miR-149* was significantly lost in 11 patient CRC tumors as compared to normal tissue (p=0.0049) as assayed by RNA-seq using TCGA analysis. Loss of miR-149* was also correlative to the staging of the tumor (data not shown). Each of the 11 patients also had significant increase in CDK4 expression with little to no change in the other markers of the CDK4/6-Rb pathway (see, FIG. 1C). As for miR-6883-5p, no data was located in TCGA. The TCGA analysis showed that RNA expression of PER1 is significantly lost in the same 50 T/N samples assayed prior (see, FIG. 1D). Thus, the in silico analysis suggests that restoring expression of miRs 6883-5p and 149* can be used as therapies in treating CRC.

Figure 1D:
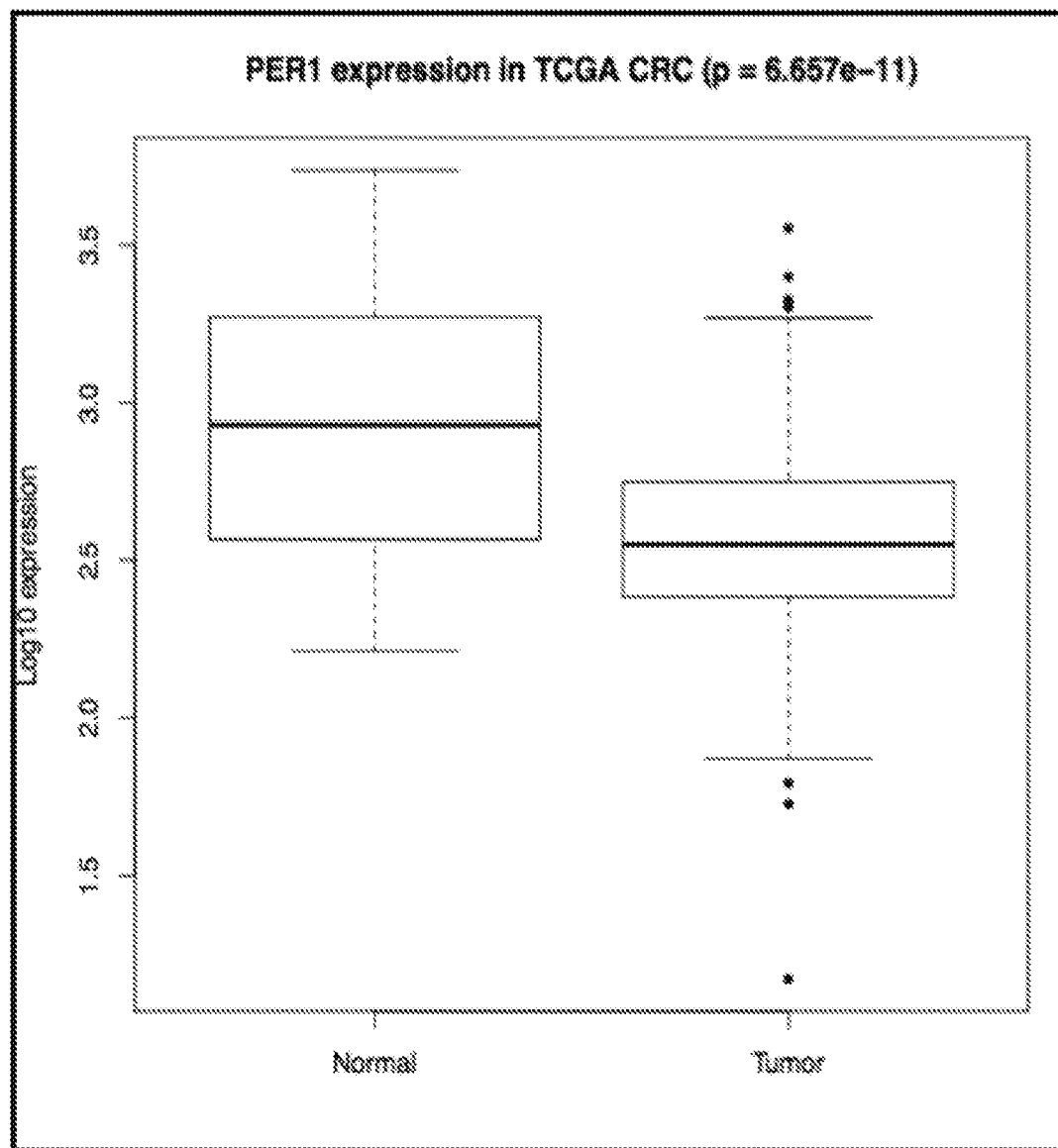

Referring in particular to FIGS. 1A, 1B, 1C, and 1D, data is presented showing that CDK4 and CDK6 are important therapeutic targets in CRC. FIG. 1A shows RNA expression data from TCGA CRC patient samples showing expression of CDK4 and CDK6 in 50 tumor and normal samples. Box plots indicate the $\log_{in}$ RNA expression of normal samples compared to tumor samples for every gene of interest. p-values were obtained from the Wilcoxon test for unpaired samples and are indicated in the figures. FIG. 1B shows Tables 1 and 2 indicating TargetScan analysis of putative binding site(s) of the family of four miRNAs in the 3'UTR regions of CDK4 and CDK6, respectively. FIG. 1C (left panel) shows a scatter plot of expression of miR-149* in 11 CRC patient tumors compared to matched normal tissue. Corresponding p-values obtained from the Wilcoxon test for paired samples is indicated. FIG. 1C (right panel) shows a histogram of CDK4/6, p16 and Rb status in the same 11 patients. FIG. 1D shows box plots showing the $\log_{10}$ RNA expression of PER1 genes in the same 50 normal samples as FIG. 1A compared to tumor samples. p-values were obtained from the Wilcoxon test for unpaired samples and are indicated.

Example 3: miR-6883-5p and miR-149* Repress Expression of CDK4 and CDK6

Figure 2A:
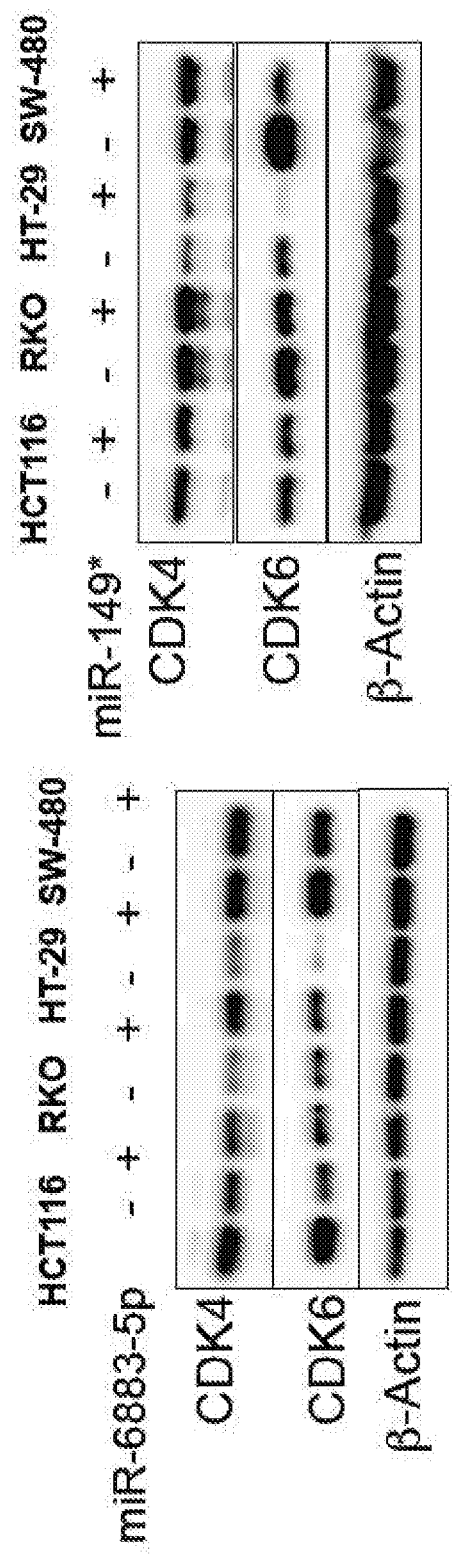
FIGS. 2A, 2B, and 2C show: CDK4 and CDK6 protein levels in a panel of CRC cell lines reverse transfected with 50 nM of miRNA mimics or scrambled duplex (SCR) for 72 hours (FIG. 2A); qRT-PCR for CDK4 and CDK6 in SCR or miRNA mimics transfected in CRC cell lines (FIG. 2B); and measured luciferase activities of HCT-116 cell stably selected with CDK4-Luciferase construct reverse transfected with either SCR or 50 nM of indicated miRNA mimics for 48 hours (FIG. 2C).
Figure 2B:
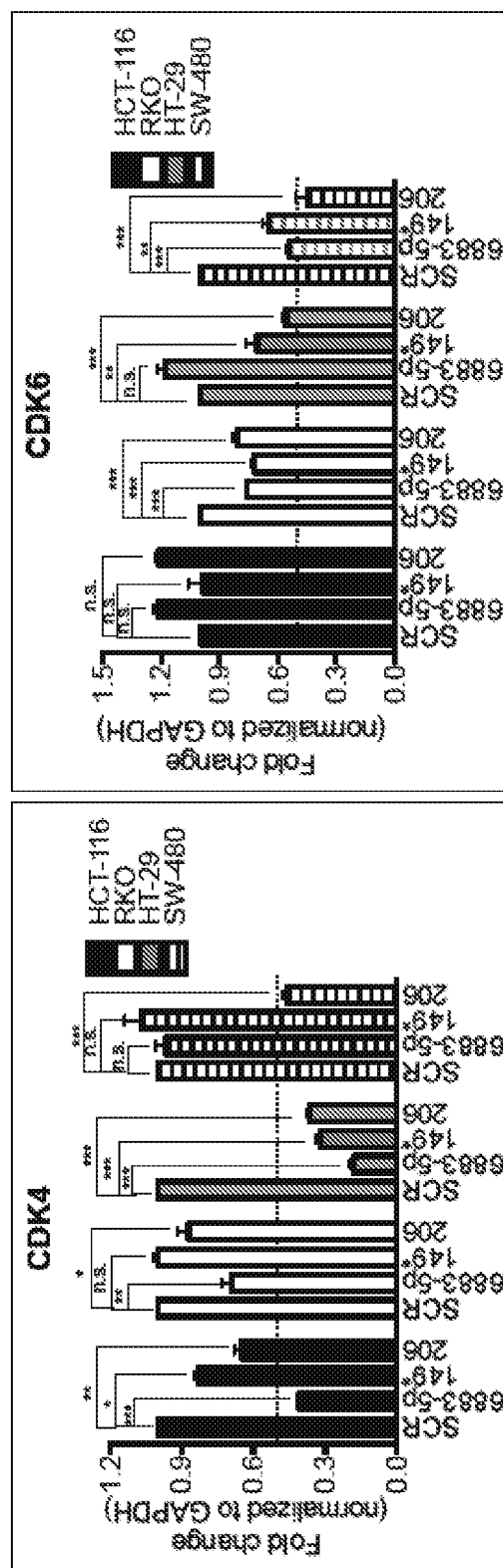
Figures 6, 7:
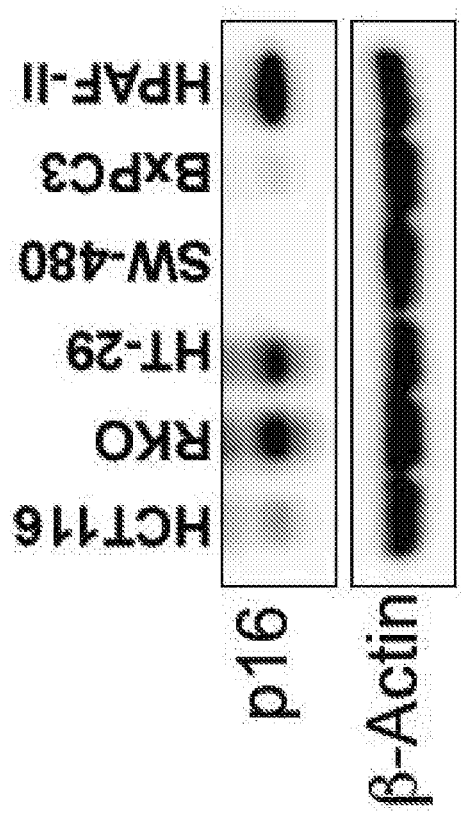
FIG. 6 shows a Western blot of the expression of p16 in CRC cell lines, and pancreatic cancer cell lines HPAF-II and BxPC3 as positive controls.
FIG. 7 shows sequence similarity of miRNA family assessed by sequence alignment using CLUSTAL-W (hsa-miR-6883-5p is SEQ ID NO: 1; hsa-miR-149-3p is SEQ ID NO: 2; hsa-miR-6785-5p is SEQ ID NO: 3; and hsa-miR-4728-5p is SEQ ID NO: 4); * marks indicate nucleotide identity.

Whether the in silico predictions regarding miR-6883-5p and miR-149* regulation of CDK4/6 translated to in vitro reults was examined A panel of CRC cell lines was used: HCT-116 (p53+/+), RKO (p53+/+), HT-29 (p53 R273H), and SW-480 (p53 R273H/P309S). All the CRC cell lines used are proficient for Rb and p16 except SW-480, which is p16−/− (see FIG. 6). Each of the cell lines was reverse transfected with both miR-6883-5p and miR-149* and examined for protein and RNA expression of CDK4 and CDK6. As shown in FIGS. 2A and 2B, miR-6883-5p targeted both CDK4 and CDK6 at both the protein and RNA level. miR-149*, on the contrary, was more potent in reducing levels of CDK6 and had no impact on CDK4. This data for potency and specificity of targeting CDKs was compared with miR-206, which has previously been reported to target CDK4 (Georgantas et al., Pigment Cell Melanoma Res., 2014, 27, 275-86). It was further confirmed using the pMirtarget-CDK4-Luciferase vector which has the CDK4 3'UTR cloned with the luciferase gene that both miR-6883-5p and miR-149* directly bind to the 3'UTR region of CDK4. As indicated in FIG. 2C, miR-6883-5p significantly reduced luciferase signal compared to miR-206 and miR-149*, respectively.

Figure 2C:
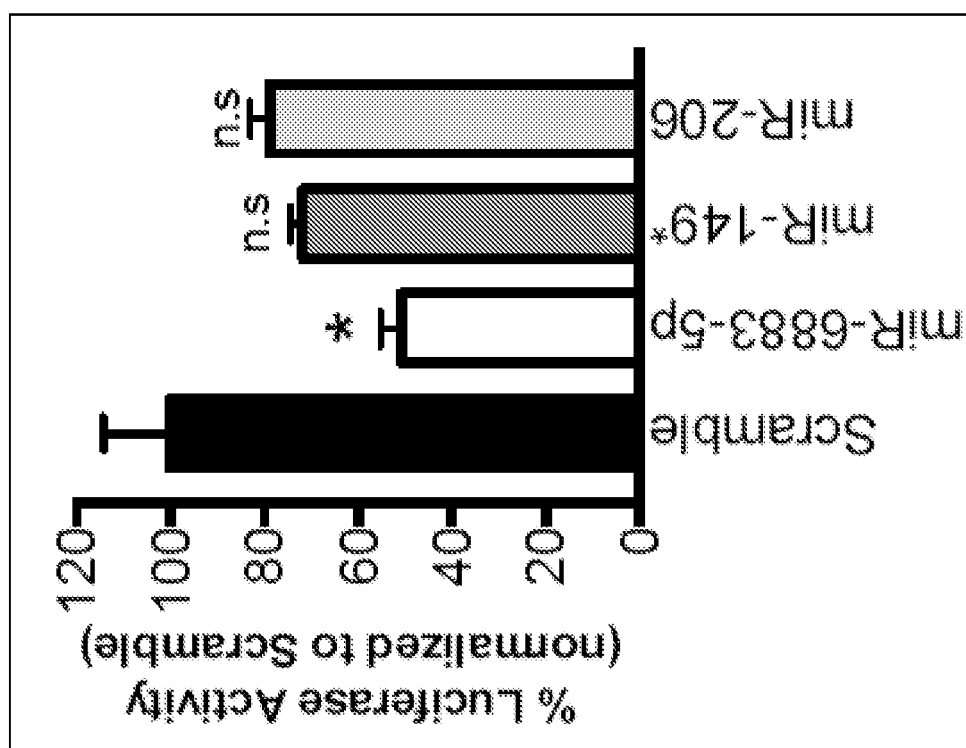

Referring in particular to FIGS. 2A, 2B, and 2C, data is presented showing that miR-6883-5p and miR-149* negatively regulate expression of CD4 and CDK6 in CRC cell lines. Referring to FIG. 2A, CDK4 and CDK6 protein levels were detected in a panel of CRC cell lines reverse transfected with 50 nM of miRNA mimics or scrambled duplex (SCR) for 72 hours. Referring to FIG. 2B, qRT-PCR was performed for CDK4 and CDK6 in SCR or miRNA mimics transfected in CRC cell lines (50 nM, 72 hours, n=3). *,  and * indicate p-value relative to SCR expression. Referring to FIG. 2C, HCT-116 cells stably selected with CDK4-Luciferase construct were reverse transfected with SCR or 50 nM of the indicated miRNA mimics for 48 hours. Measured luciferase activities were normalized per μg of protein for indicated samples and reported as RLU±SEM (n=3). * indicates p-value relative SCR RLU.

Figure 3A:
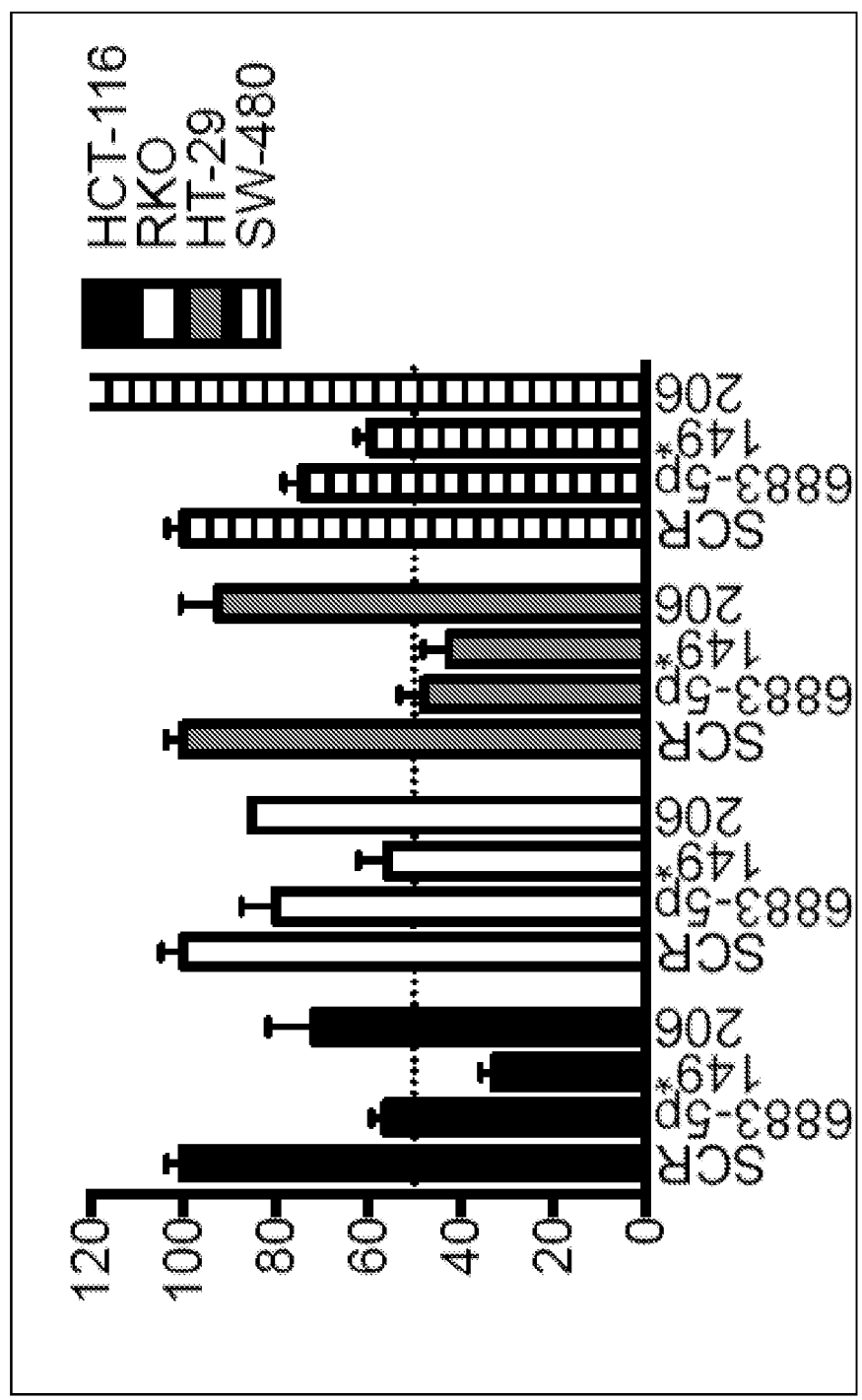
FIGS. 3A, 3B, 3C, 3D, and 3E show: effects on cell viability measured 72 hours post-transfection of CRC cell lines reverse transfected with either 50 nM SCR or 50 nM of indicated miRNA mimics using CellTiter-Glo assay Z (FIG. 3A); effects of miRNA mimics on long-term cell proliferation of CRC cell lines reverse transfected with 100 nM of SCR or indicated miRNA mimic assessed by colony formation assays; representative images of cells stained with crystal violet are shown (left panel) and relative colony number is represented graphically (right panel) (FIG. 3B); representative western blots showing effects on cell cycle markers (FIG. 3C) and markers of apoptosis (FIG. 3D); and representative results of changes in G1 and sub-G1 phases of cell cycle and apoptotic cells assessed in three CRC cell lines reverse transfected with either SCR or 50 nM (HCT-116 and HT-29) or 100 nM (RKO) miRNA mimics (FIG. 3E).

Example 4: Restoring Expression of miR-6883-5p and miR-149* Results in $G_1$-Arrest and Cel Death Given the ability to target CDK4/6, the functional consequences of restoring the expression of miRs-6883-5p and 149* as compared to miR-206 in the panel of CRC cell lines was determined. Since the miRNAs target proteins in the cell cycle, it was believed that they could affect cell proliferation, both short-term and long-term. As shown in FIG. 3A, all three miRNAs had comparable and moderate short-term anti-proliferative effect on the panel of CRC cell lines as measured by cell viability, 72 hours post-transfection. There was greater than 50-70% inhibition on the long-term proliferation of these cells as seen from colony formation assay in all four cell lines (see, FIG. 3B). The effects of the miRNAs on the cell cycle markers were also examined to determine whether the inhibition of CDK4/6 would lead to $G_1$-arrest in all the cell lines. As shown in FIG. 3C, in all four cell lines, miR-6883-5p and miR-149* reduced levels of phosphorylated Rb (S795), indicating $G_1$-arrest and inhibition of CDK4/6 activity. These findings were further confirmed by PI-staining and looking at the cell cycle profiles of each of these cell lines. As shown in FIG. 3E, both RKO and HT-29 cells showed $G_1$-arrest on transfection with each of the miRNAs and a small fraction of cells underwent cell death.

However, in HCT-116 alone, expression of all miRNAs led to apoptosis, with between 30-50% cells in sub-G1 phase. This result further replicated with the PARP-cleavage data seen in FIG. 3D. While in HCT-116 cell lines, all three miRNAs induced increased apoptosis; in RKO and SW-480 cells, 6883-5p was the most potent in inducing apoptosis. No change in the p53 levels indicated that apoptosis was not p53-dependent in p53+/+ cells. Interestingly, miR-6883-5p downregulated XIAP and $BCL_{xL}$, which in part could explain the induction of apoptosis by miR-6883-5p. While XIAP is a predicted target of the family of miRNAs, $BCL_{XL}$ is not. However, both $BCL_{XL}$ and XIAP contribute to the pro-apoptotic effects of the miRs.

Figure 3B:
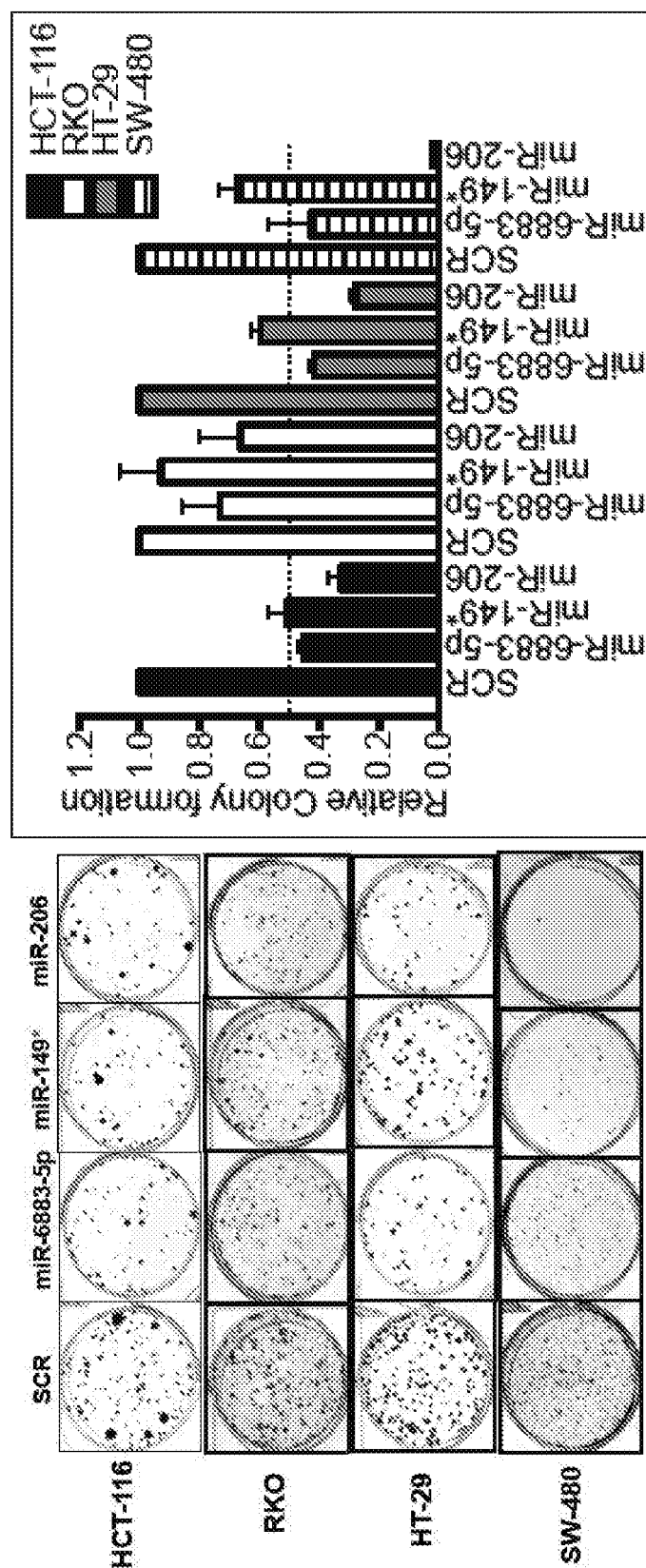
Figure 3C:
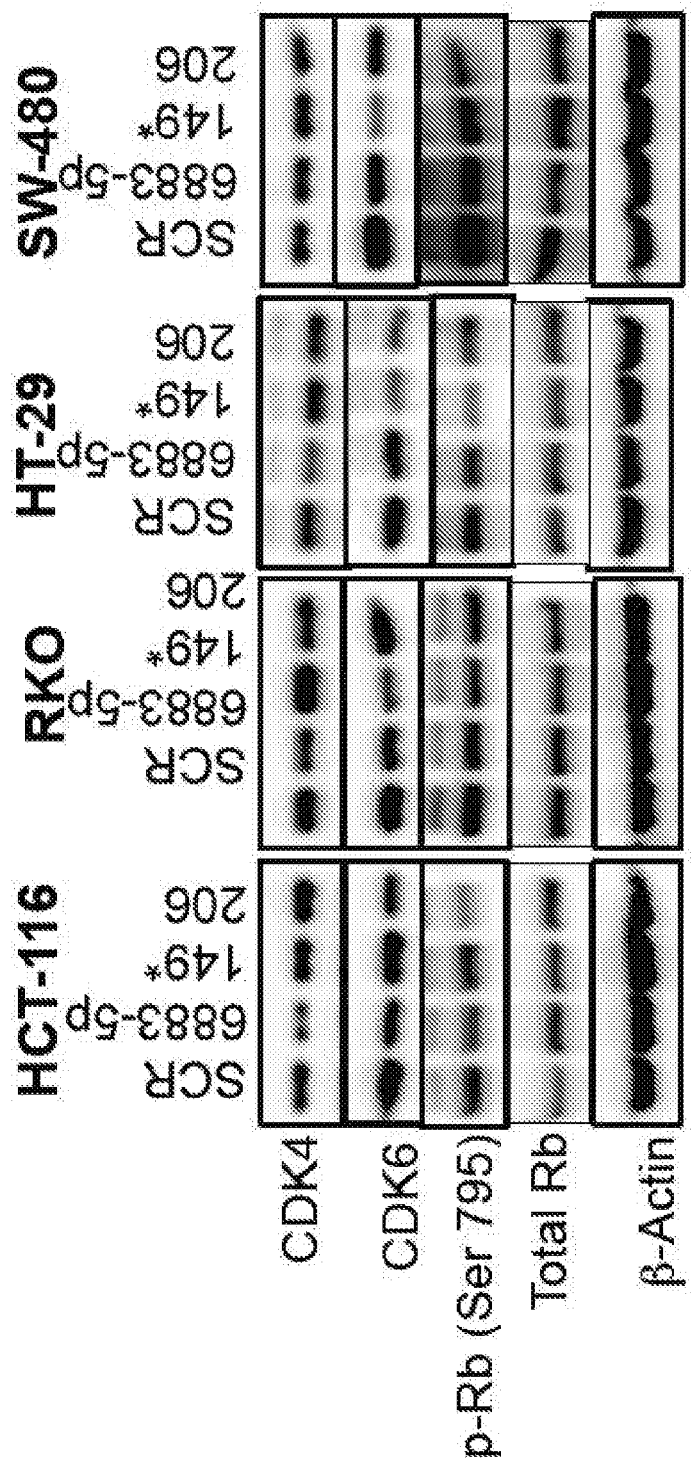
Figure 3D:
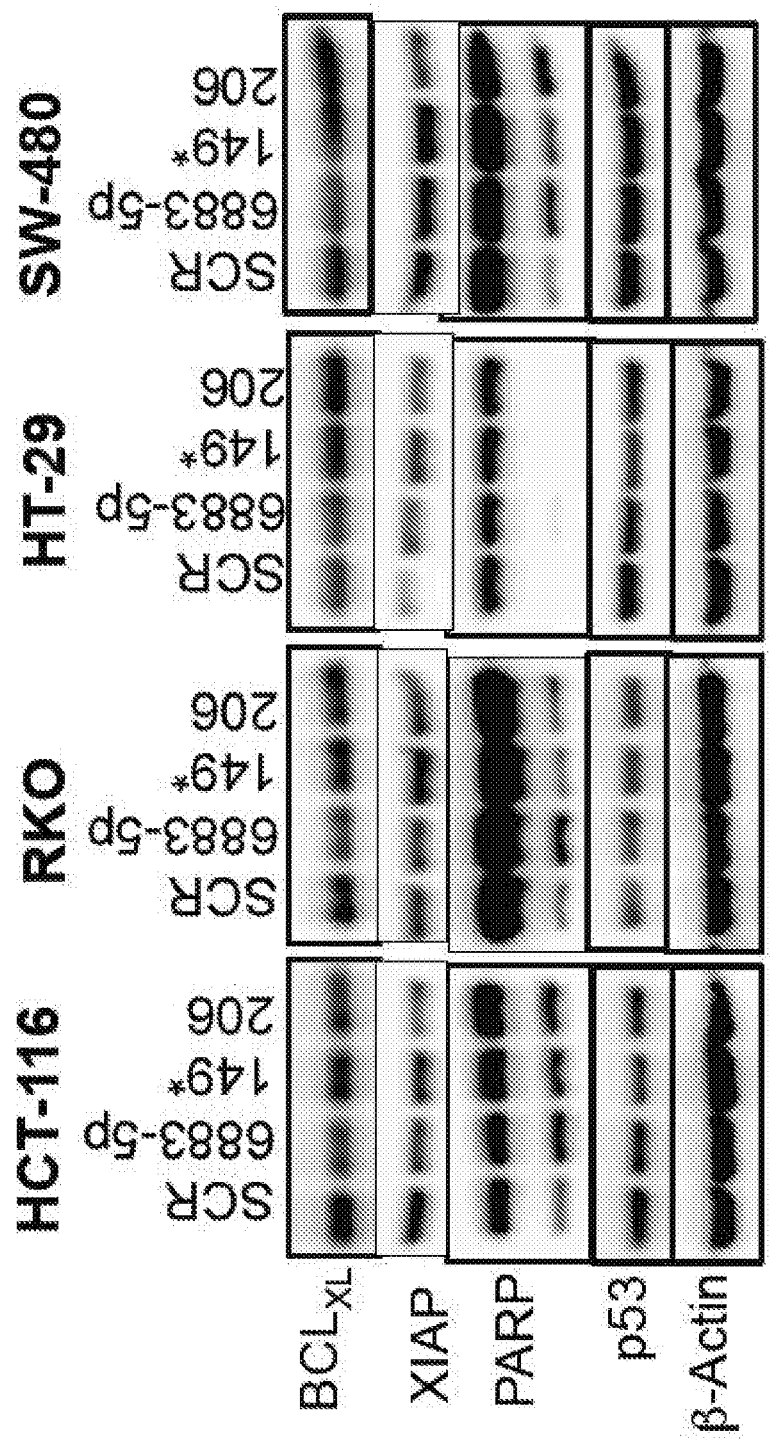
Figure 3E:
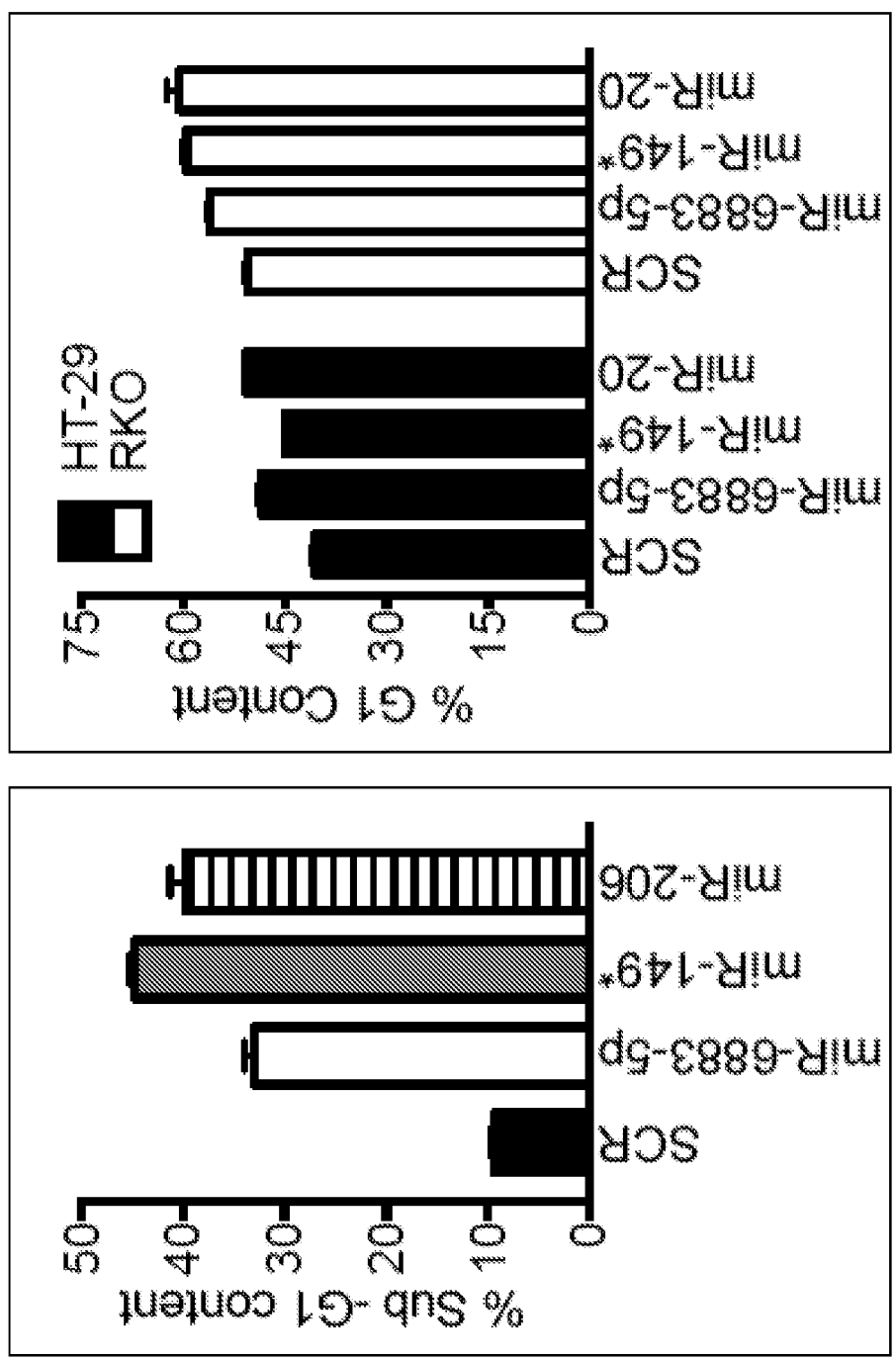

Referring in particular to FIGS. 3A, 3B, 3C, 3D, and 3E, data is presented showing that restoring expression of miR-6883-5p and miR-149* results in $G_1$-arrest and cell death in CRC cell lines. Referring to FIG. 3A, a panel of CRC cell lines was reverse transfected with 50 nM SCR or 50 nM of indicated miRNA mimics. The effects on cell viability were measured 72 hours post-transfection using CellTiter-Glo assay. Referring to FIG. 3B, the effects of the miRNA mimics on long-term cell proliferation of CRC cell lines was assessed by colony formation assays performed in 6-well plates. Cells were reverse transfected with 100 nM of SCR or indicated miRNA mimic After 72 hours, 500 cells were seeded per well in triplicate for each condition and stained with crystal violet on Day 14. Representative images of cells stained with crystal violet are shown (left panel) and relative colony number (n=3) is represented graphically (right panel). All four CRC cell lines were reverse transfected with 100 nM SCR or indicated miRNA mimics. The effects on cell cycle markers (see, FIG. 3C) and markers of apoptosis (see, FIG. 3D) were evaluated by western blot 72 hours post-transfection. Representative western blots are shown (n=3). Referring to FIG. 3E, cell cycle profiles and apoptotic cells were assessed in three CRC cell lines by reverse transfecting with SCR or 50 nM (HCT-116 and HT-29) or 100 nM (RKO) miRNA mimics 72 hours post-transfection, cells were fixed, stained with PI, and analyzed by FACS. Representative results of changes G1 and sub-G1 phases of cell cycle are graphically represented (n=3).

Figure 4A:
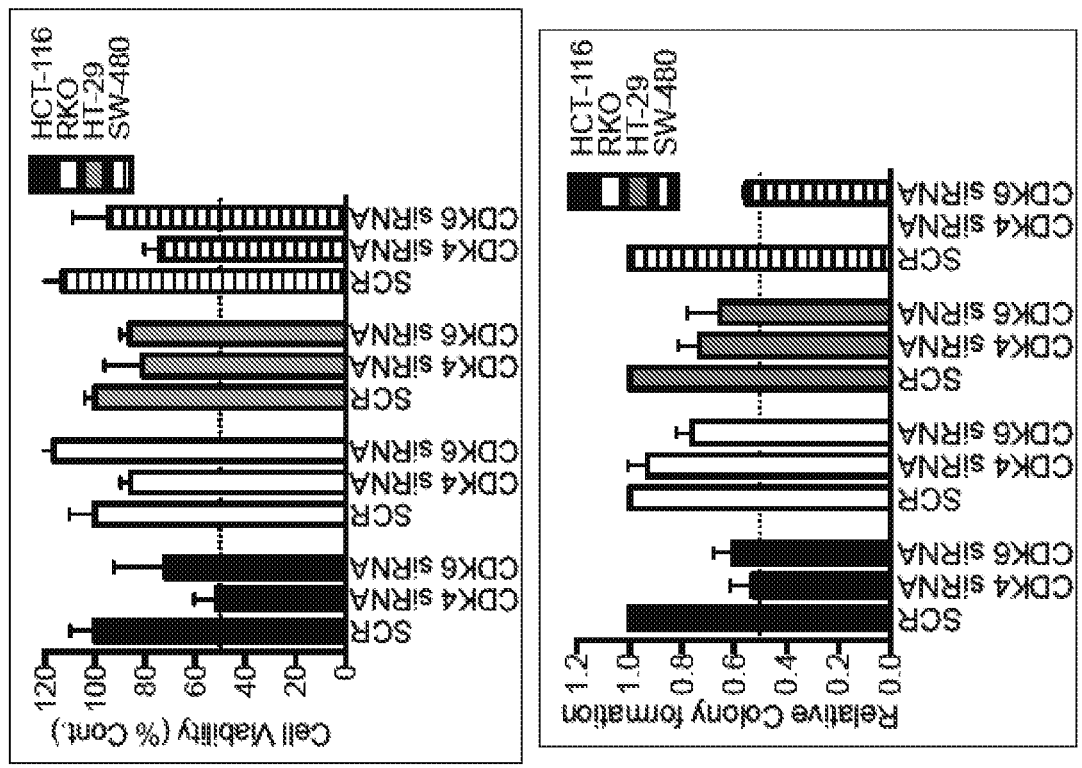
FIGS. 4A, 4B, 4C, and 4D show: effects of short-term cell proliferation of four CRC cell lines reverse transfected with SCR or 80 nM of CDK4 or CDK6 siRNA measured 72 hours post-transfection using CellTiter-Glo assay (FIG. 4A); representative images of cells reverse transfected with 80 nM CDK4 or CDK6 and stained with crystal violet (FIG. 4B); representative western blots of four CRC cell lines reverse transfected with 80 nM CDK4 or CDK6 siRNA (FIG. 4C); and representative results of changes G1 and sub-G1 phases of cell cycle and apoptotic cells assessed in three CRC cell lines by reverse transfecting with SCR or 40 nM (HCT-116) or 80 nM (HT-29 and RKO) siRNA of CDK4 and CDK6 (FIG. 4D).
Figure 4B:
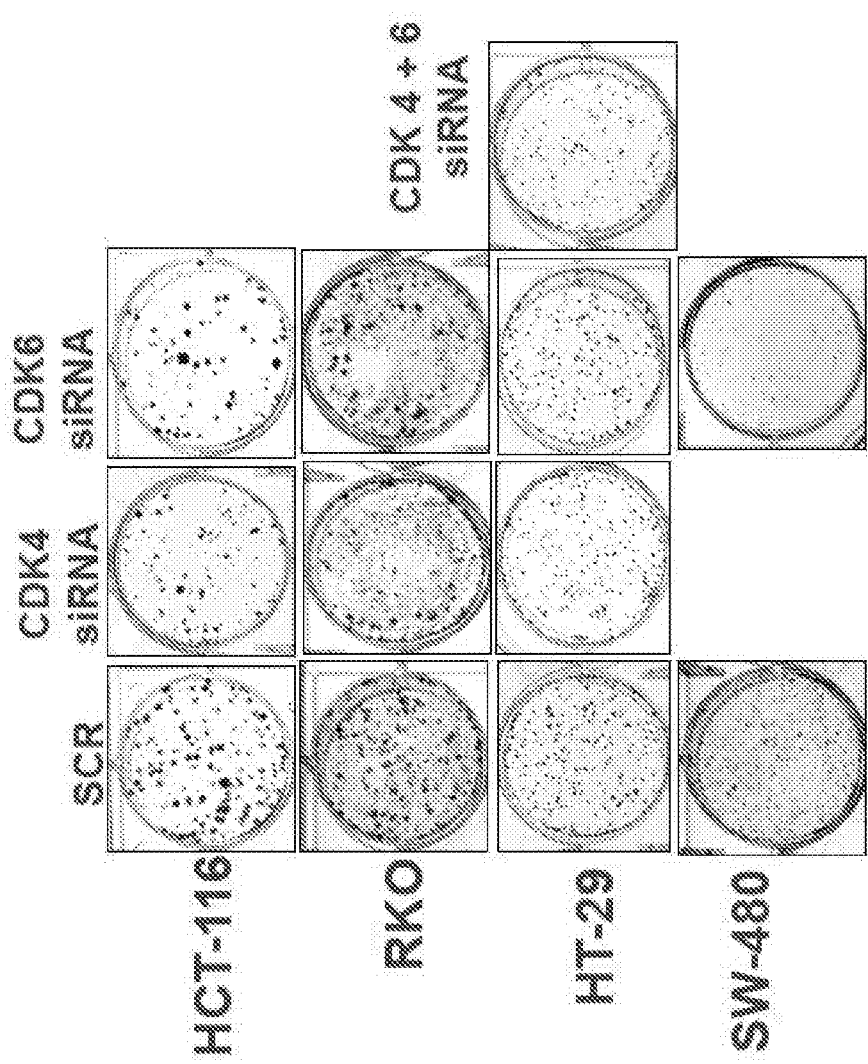

Example 5: Silencing of CDK4 and CDK6 Phenocopies the Effects of miR-6883-5p and miR-149* Mimics in CRC Cell Lines To determine whether the biological effects of miR-6883-5p and miR-149* could be attributed to the direct targeting of CDK4/6, the expression of CDK4/6 was silenced by siRNA and the associated functional consequences were detected. As shown in FIG. 4A, knockdown of CDK4 and CDK6 had similar effects on short-term proliferation of CRC cell lines as with overexpression of miRNAs. However, silencing the expression of CDK4/6 was less potent in preventing long-term proliferation of CRC cell lines, especially RKO and HT-29, as seen in FIG. 4B. This indicates that targeting of CDK4/6 by miR-6883-5p and miR-149* can only, in part, explain the anti-proliferative effects of these miRNAs. Knockdown of CDK4 and CDK6 siRNAs arrested cells in $G_1$ phase of cell cycle (see, FIGS. 4C and 4D). However, unlike the miRNAs, knockdown of CDK4 alone lead to cell death HCT-116 and SW-480 cells. Given the leakiness of the CDK4 siRNA, knockdown of both CDK4 and CDK6 is more potent and needed to induce apoptosis in CRC cell lines compared to either gene alone. Thus, the dual targeting of CDK4 and CDK6 by miRNAs has therapeutic benefits in CRC cell lines.

Figure 4C:
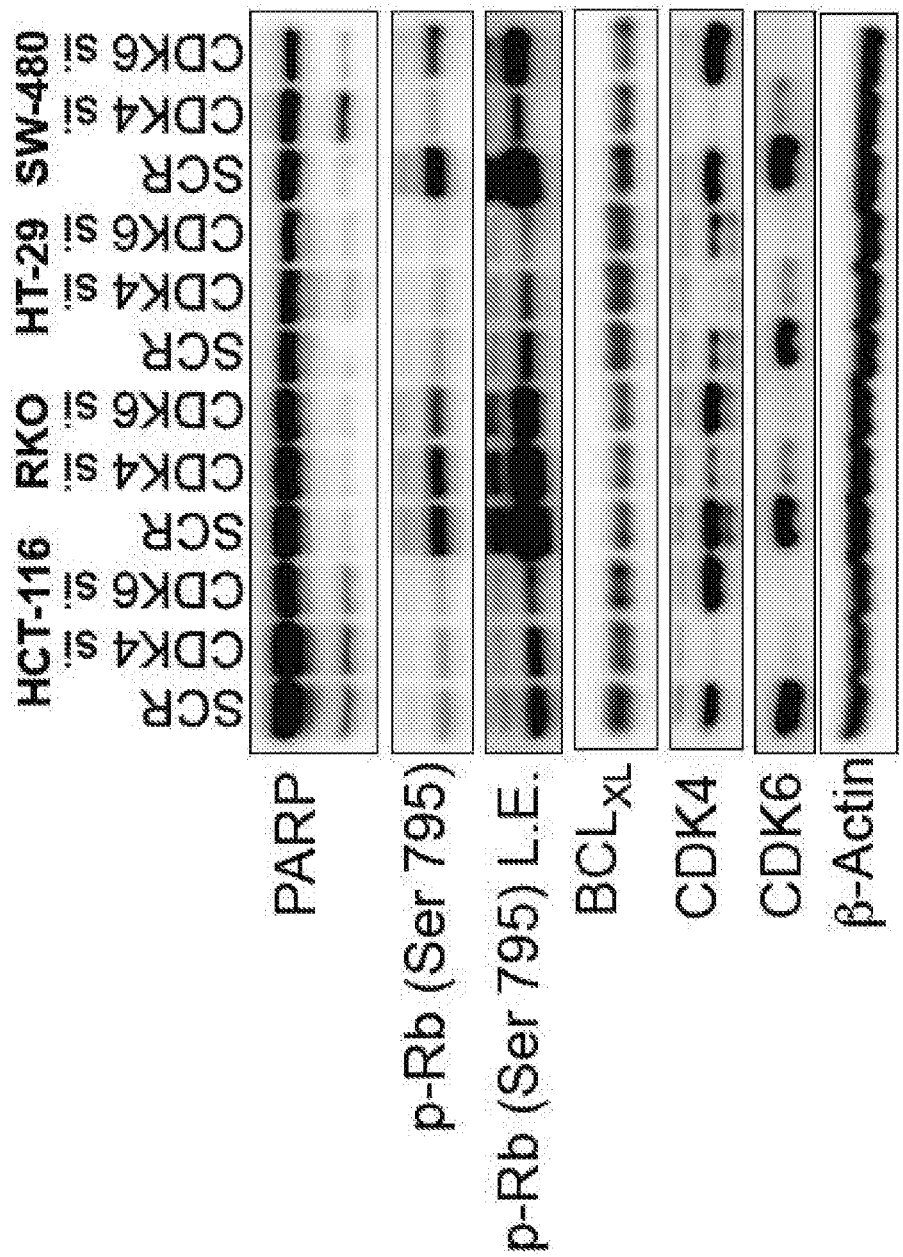
Figure 4D:
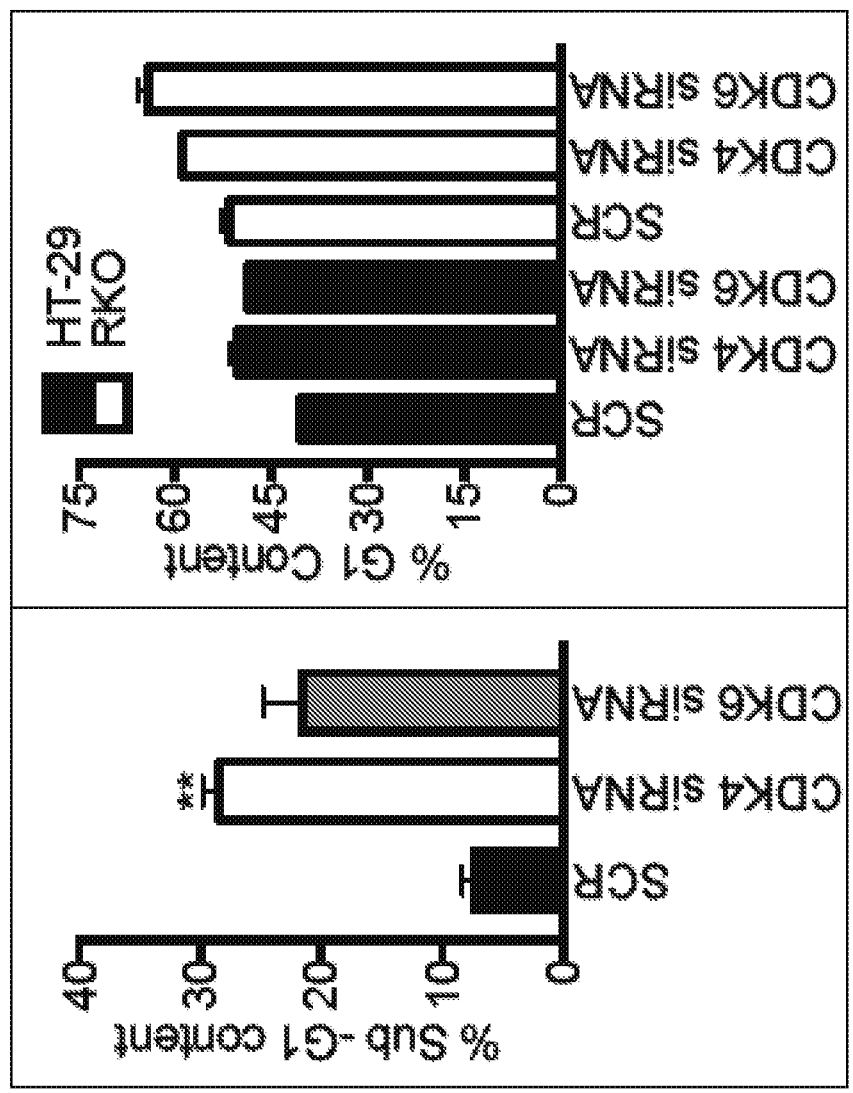

Referring in particular to FIGS. 4A, 4B, 4C, and 4D, the effect of silencing of CDK4 and CDK6 phenocopies on miRNA mimics is shown. Referring to FIG. 4A, all four CRC cell lines were reverse transfected with SCR or 80 nM of CDK4 or CDK6 siRNA. The effects of short-term cell proliferation were measured 72 hours post-transfection using CellTiter-Glo assay. Referring to FIG. 4B, the long-term effects on cell proliferation by silencing CDK4 or CDK6 were assessed by a colony formation assay performed in 6-well plates. All four cell lines were reverse transfected with 80 nM CDK4 or CDK6. At 72 hours post-transfection, 500 cells were seeded per well in triplicate and stained with crystal violet on Day 14. Representative images of cells stained with crystal violet are shown (left panel) and relative colony number (n=3) is represented graphically (right panel). Referring to FIG. 4C, all four CRC cell lines were reverse transfected with 80 nM CDK4 or CDK6 siRNA. The effects on markers of cell cycle and apoptosis were evaluated by western blot 72 hours post-transfection. Representative western blots are shown (n=3). Referring to FIG. 4D, cell cycle profiles and apoptotic cells were assessed in three CRC cell lines by reverse transfecting with SCR or 40 nM (HCT-116) or 80 nM (HT-29 and RKO) siRNA of CDK4 and CDK6. 72 hours post-transfection, cells were fixed, stained with PI, and analyzed by FACS. Representative results of changes G1 and sub-G1 phases of cell cycle are graphically represented (n=3).

Figure 5A:
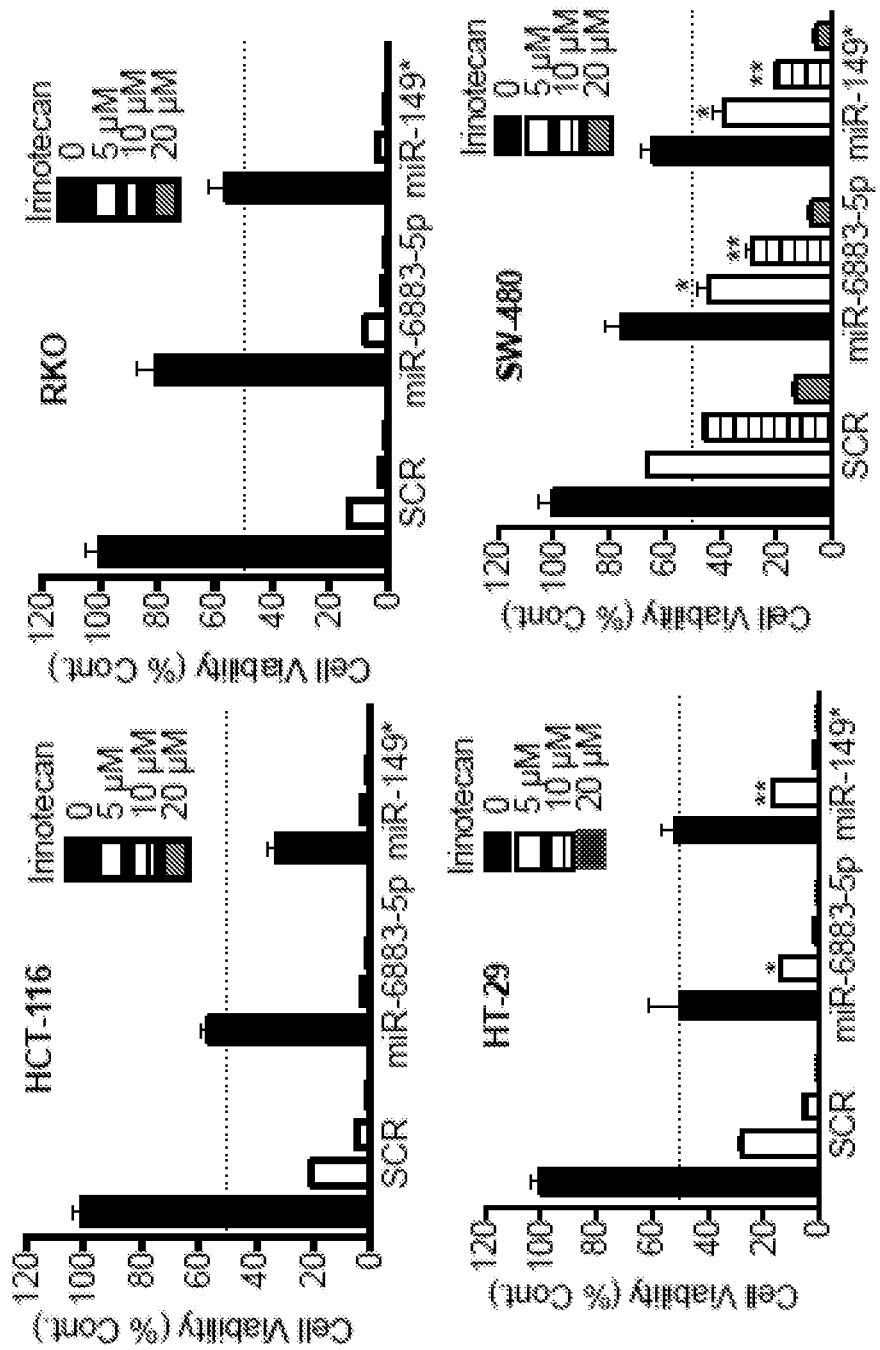
FIGS. 5A, 5B, 5C, and 5D show: cell viability 72 hours post-transfection of a panel of CRC cell lines reverse transfected with 25 nM (HCT-116) or 50 nM of SCR or indicated miRNA mimics, with addition of the indicated doses of Irinotecan (FIG. 5A) or 5-FU (Figure B), using the CellTiter-Glo assay; and representative western blots of cells treated with 50 nM of miRNA mimic and Irinotecan (FIG. 5C) or 5-FU (FIG. 5D) showing the effect on apoptosis and cell cycle markers.
Figure 5B:
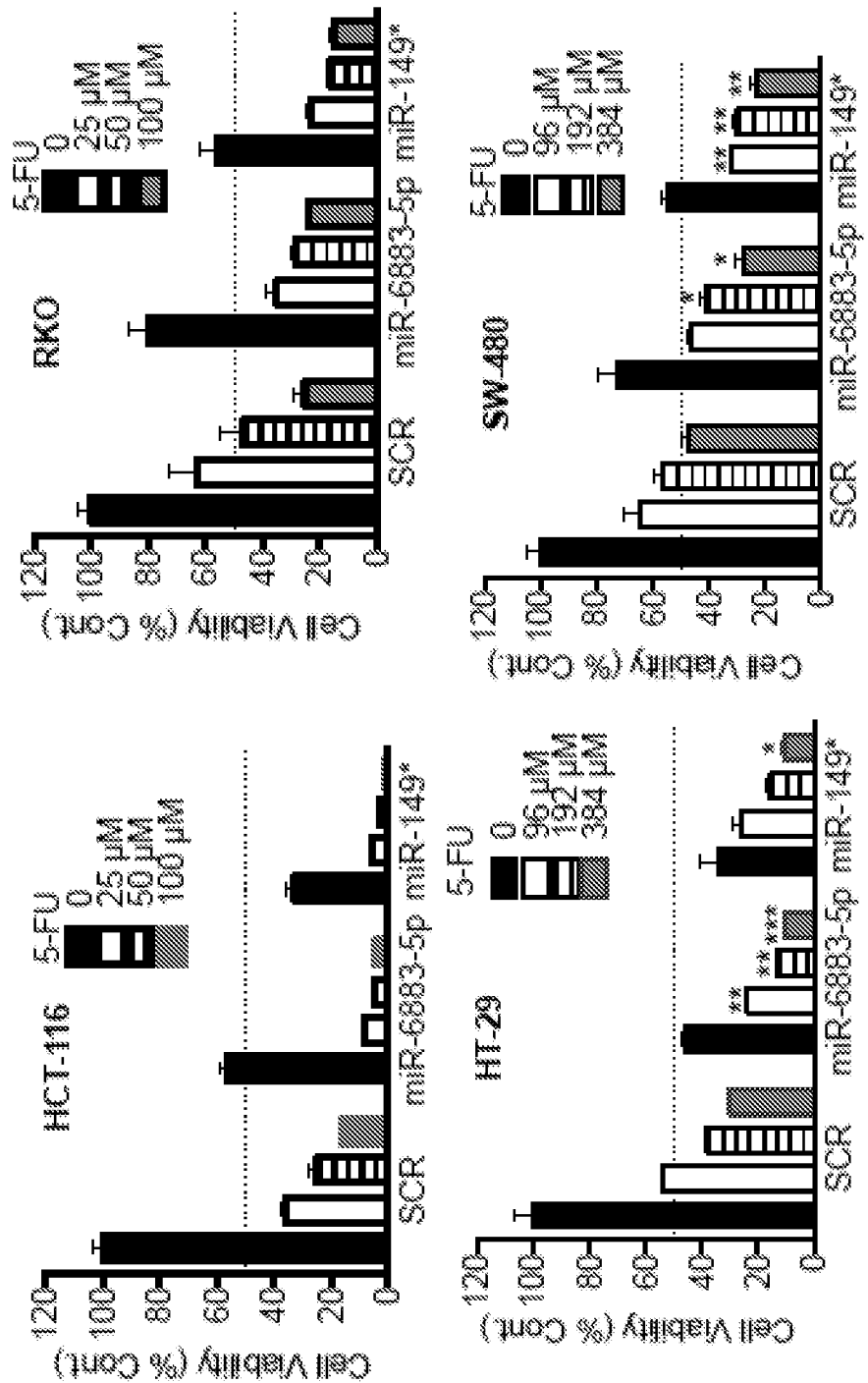

Example 6: miR-6883-5p and miR-149* Synergize with FDA-Approved Therapeutics for CRC The combinatorial effect of miR-6883-5p and miR-149* with frontline therapeutics Irinotecan and 5-FU was evaluated. As shown in FIG. 5A, both miR-6883-5p and miR-149* synergized with Irinotecan in all four cell lines. Further, both the miRNAs also increased the sensitivity of p53 mutant cell lines HT-29 and SW-480 to 5-FU (see, FIG. 5B). The synergistic combinations led to cell death in all four cell lines as measured by PARP cleavage (see, FIGS. 5C and 5D). The Irinotecan-miRNA combination engaged the intrinsic pathway of cell death as measured by Cleaved Caspase-9, BCL, and XIAP (see, FIG. 5C). In cells treated with 5-FU, single agent miR-149* and 5-FU caused cell cycle arrest in, as seen by p21 levels. The combination however, led to apoptosis (see FIG. 5D). Thus, both miR-6883-5p and miR-149* are combination agents in CRC.

Figure 5C:
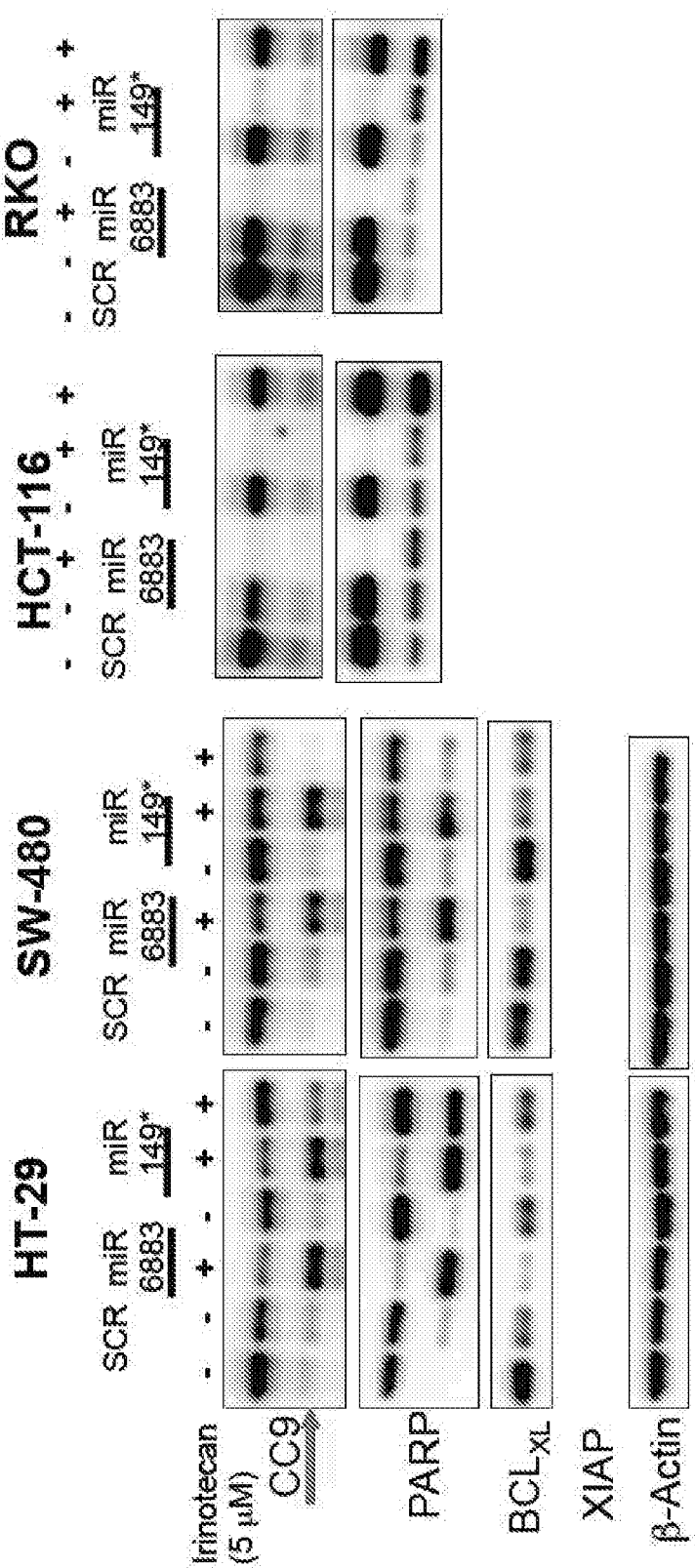
Figure 5D:
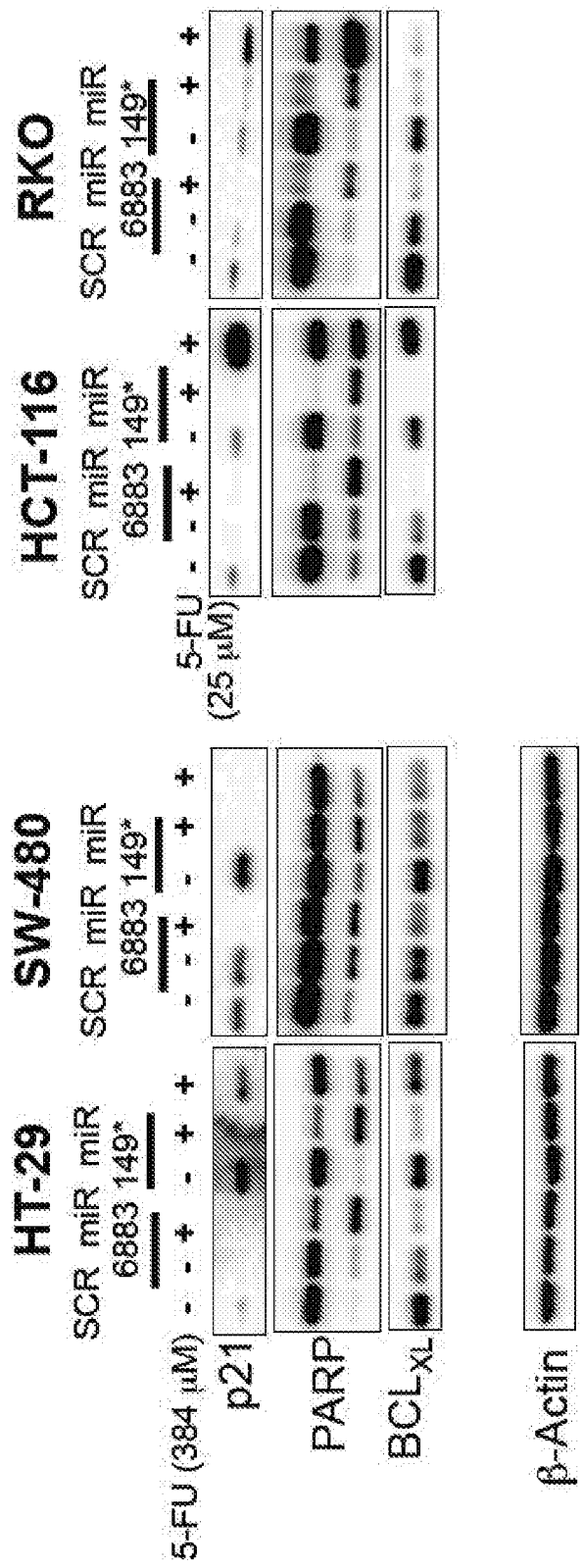

Referring in particular to FIGS. 5A, 5B, 5C, and 5D, data is presented that demonstrates that miR-6883-5p and miR-149* synergize with Irinotecan and 5-FU in CRC cell lines. A panel of CRC cell lines was reverse transfected with 25 nM (HCT-116) or 50 nM of SCR or indicated miRNA mimics. At 16 hours post-transfection, Irinotecan (see, FIG. 5A) or 5-FU (see, FIG. 5B) at indicated doses were added. Synergy of miRNA-drug was measured by cell viability 72 hours post-transfection using CellTiter-Glo assay. The effect on apoptosis and cell cycle markers with miRNA alone or combination were assessed using 50 nM of miRNA mimic and 5 μM (HT-29 and SW-480) or 2.5 μM Irinotecan (HCT-116 and RKO) by western blot. For 5-FU, 384 μM (HT-29 and SW-480) and 25 μM (HCT-116 and RKO) were used. Representative western blots are shown in FIG. 5C and FIG. 5D, respectively.

Example 7: Efficacy in Cell Lines

Figure 8:
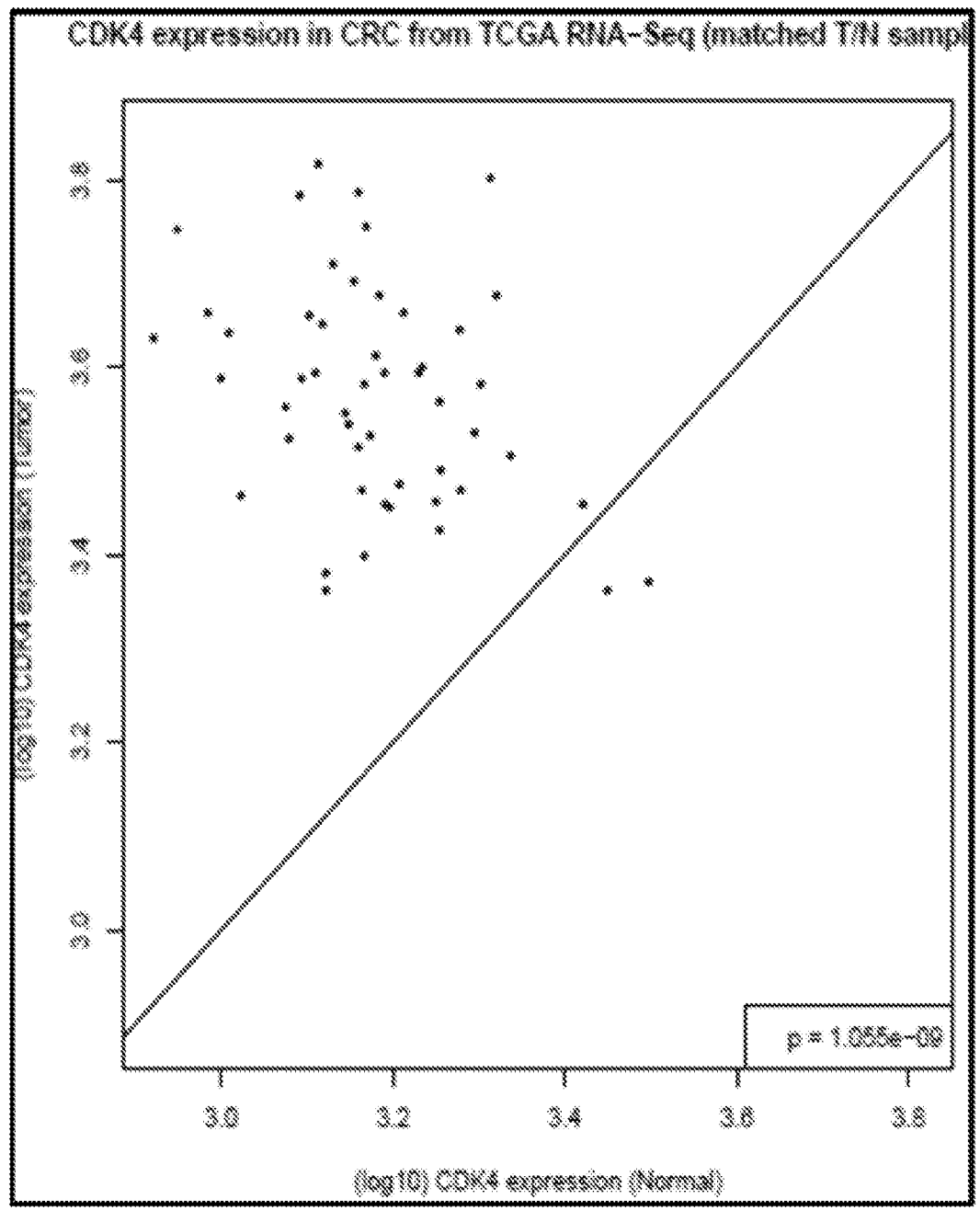
FIG. 8 shows RNA expression data from TCGA CRC patient samples showing expression of CDK4, CDK6 and PER1 in matched 50 tumor and normal samples; scatter plots indicate the $\log_{10}$ RNA expression of normal samples compared to tumor samples for the indicated gene of interest; p-values were obtained from the Wilcoxon test for paired samples and are indicated.
Figure 8:
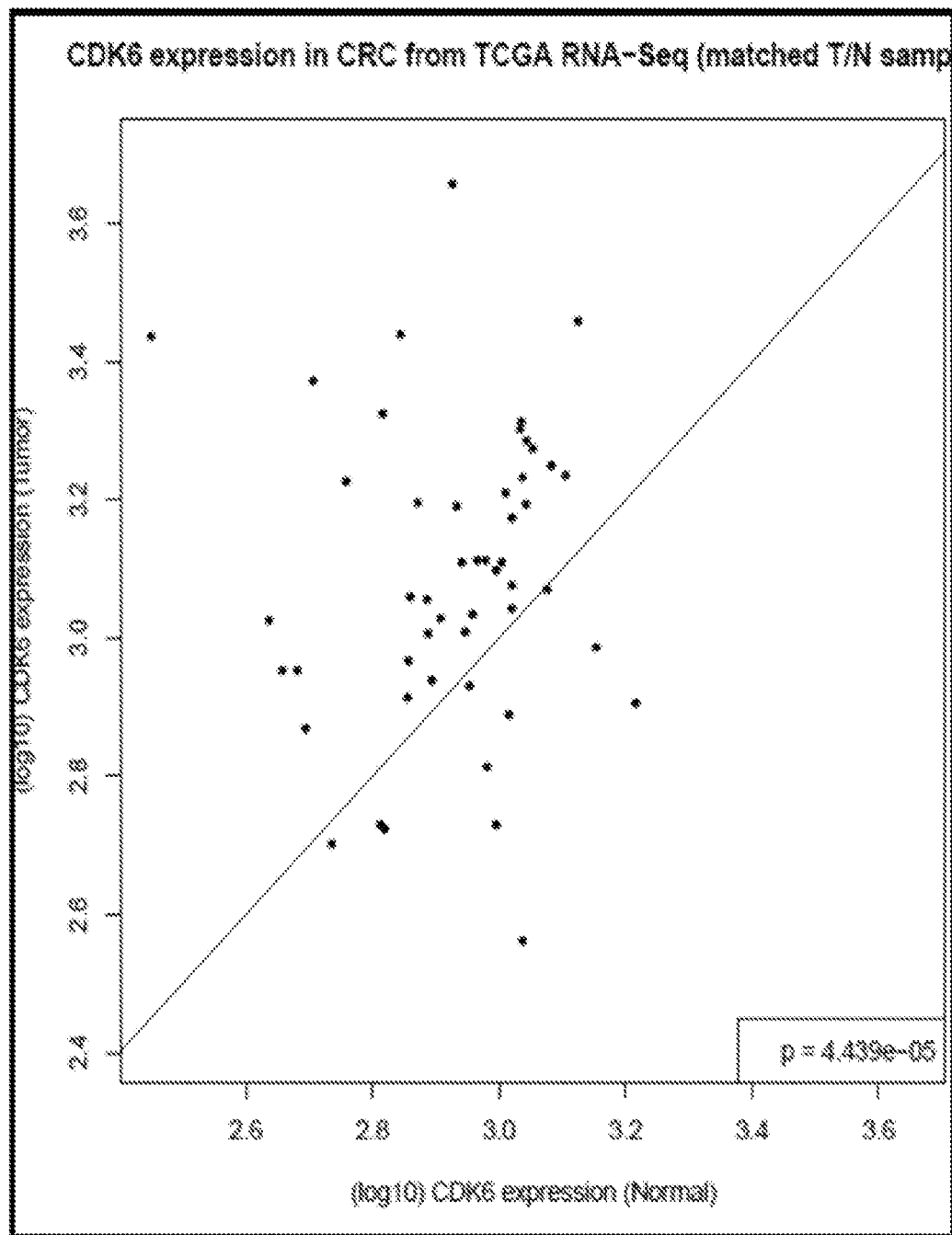
Figure 8:
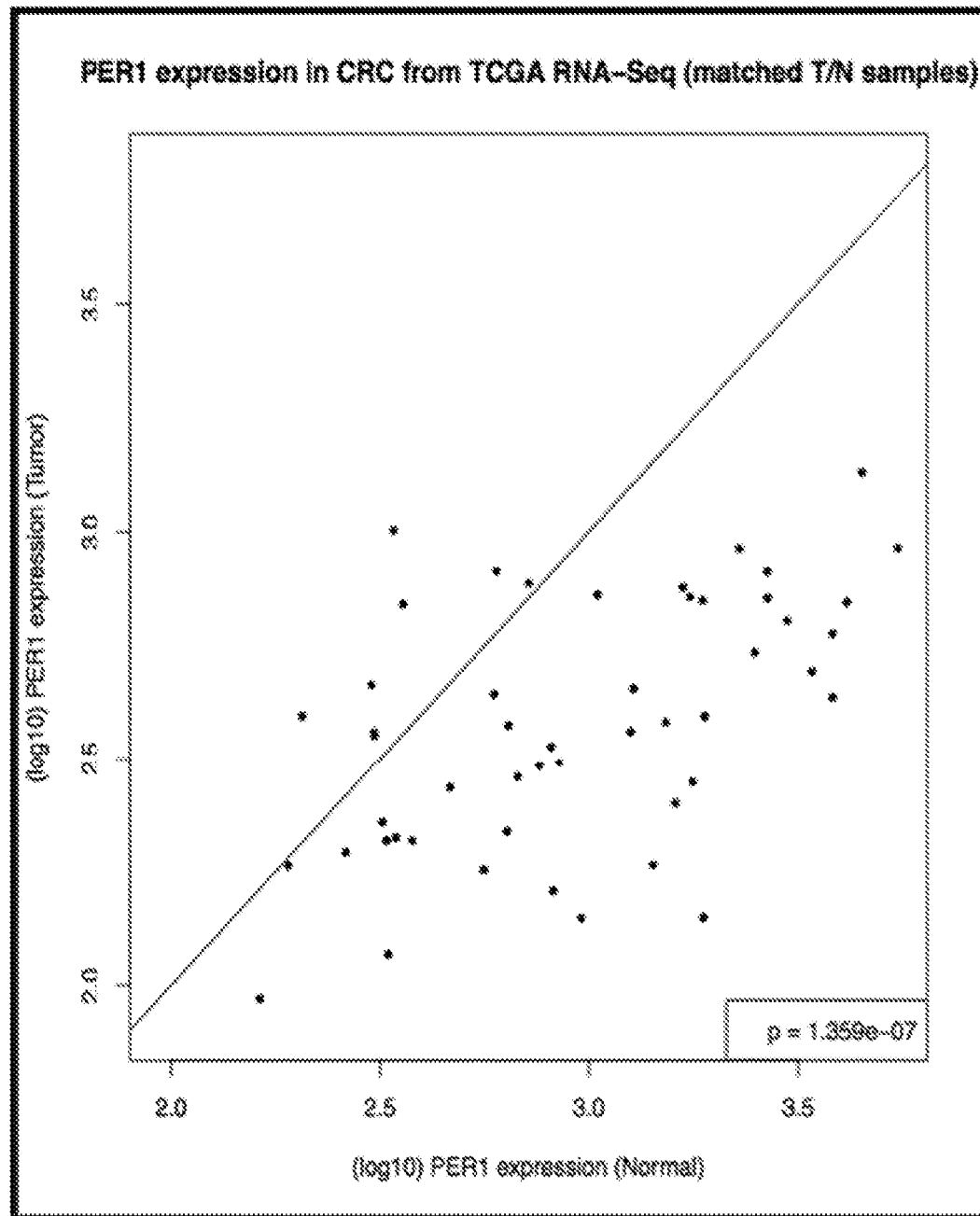

RNA expression data for CDK4, CDK6 and PER1 was obtained from TCGA CRC patient samples in 50 matched tumor and normal samples (see, FIG. 8). The scatter plots indicate the $\log_{10}$ RNA expression of normal samples compared to tumor samples for the indicated gene of interest. p-values were obtained from the Wilcoxon test for paired samples and are indicated.

Figure 9:
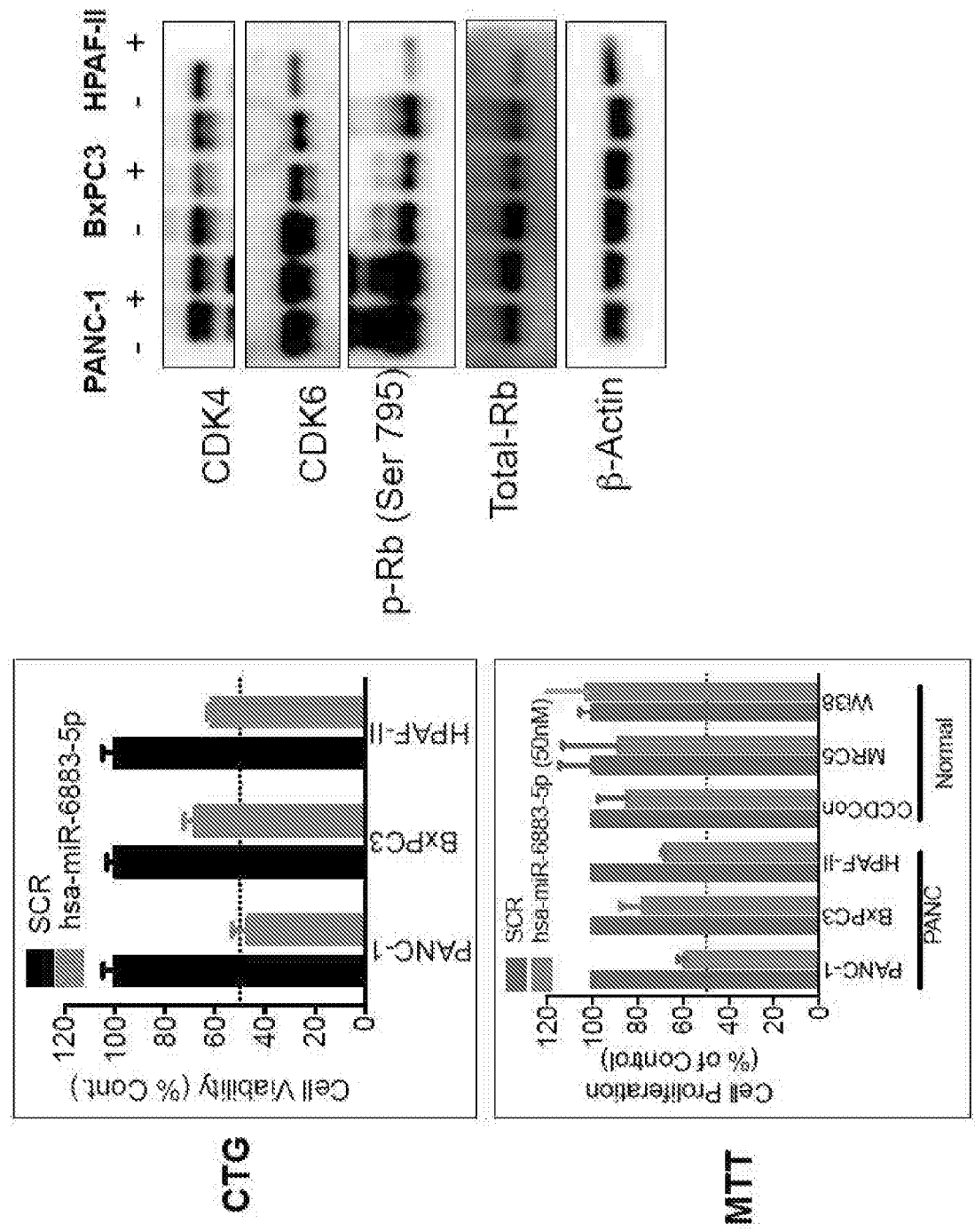
FIG. 9 shows cell viability, cell proliferation, and western blot analysis of pancreatic cancer cell lines treated with SCR or the indicated miRNA.
Figure 10:
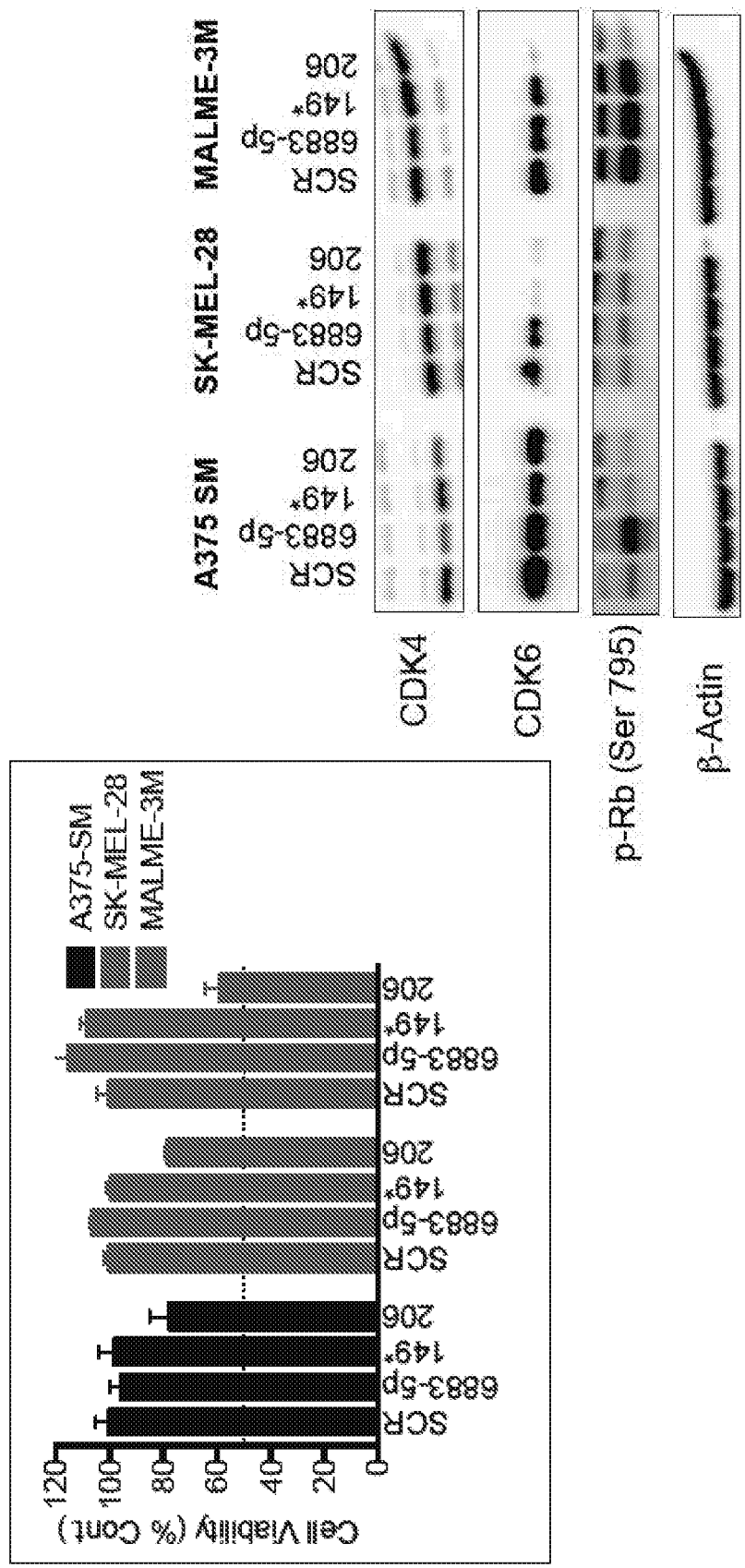
FIG. 10 shows cell viability and western blot analysis of melanoma cancer cell lines treated with SCR or the indicated miRNA.
Figure 11:
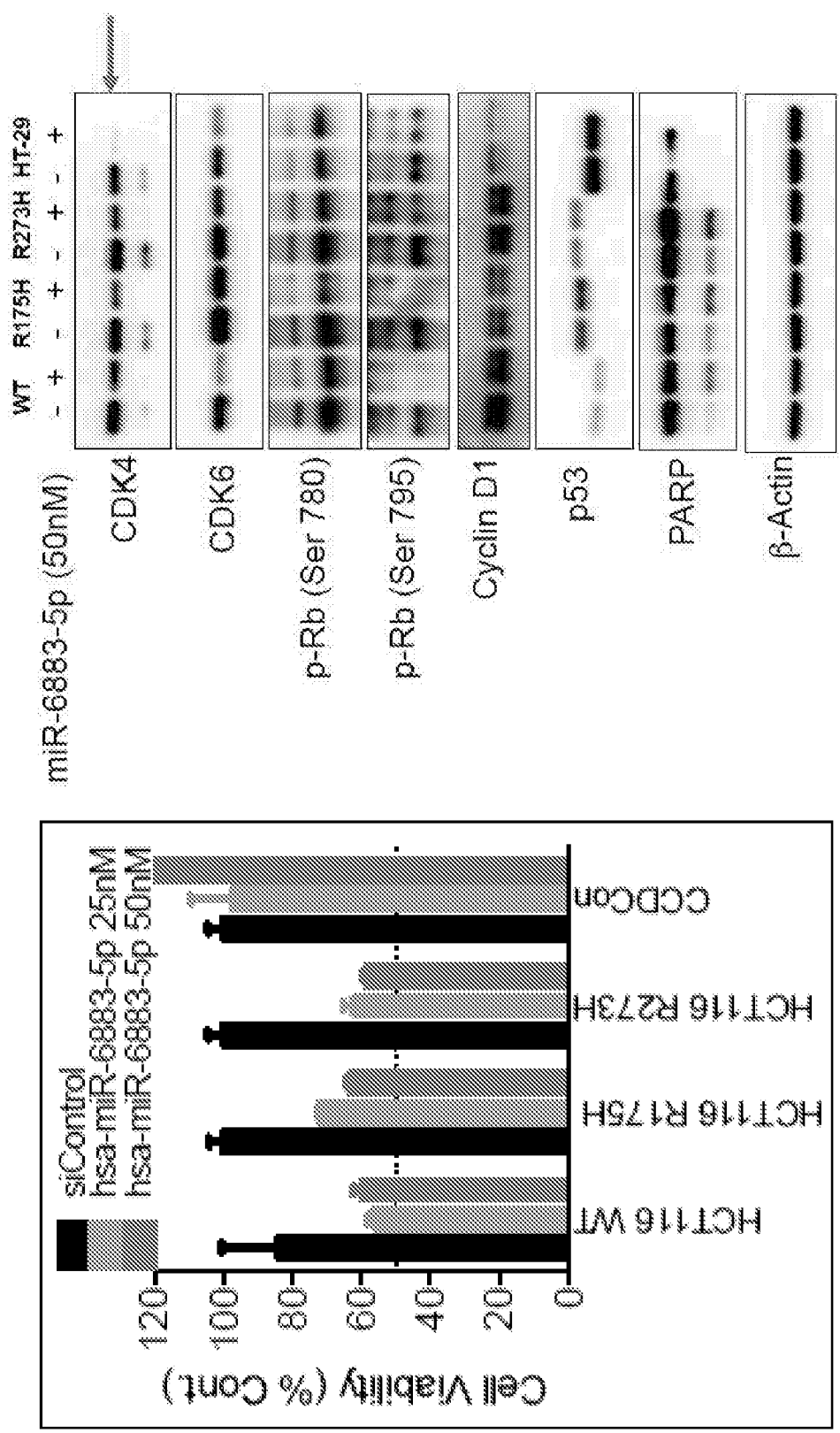
FIG. 11 shows cell viability and western blot analysis of the induction of G1-cell cycle arrest by targeting CDK4 and CDK6, independent of p53 status.

Cell viability, cell proliferation, and Western blot analysis of pancreatic cancer cell lines treated with SCR or the indicated miRNA was examined (see, FIG. 9). Cell viability, cell proliferation, and Western blot analysis of melanoma cancer cell lines treated with SCR or the indicated miRNA was also examined (see, FIG. 10). In addition, cell viability and Western blot analysis of the induction of G1-cell cycle arrest by targeting CDK4 and CDK6, independent of p53 status, was also examined (see, FIG. 11).

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety. The subject matter described herein was made with government support under Grant Nos. R01 CA 176289 and P30 CA 006927 awarded by The National Institutes of Health (NIH).

What is claimed is:

1. A method for treating colorectal cancer comprising administering to a subject in need thereof one or more oligonucleotides consisting of 15 to 40 linked nucleobases, or a salt thereof, that comprises a nucleobase sequence that is at least 80% identical to a nucleobase sequence of hsa-miR-6883-5p.

2. The method according to claim 1, wherein the one or more oligonucleotides is a modified oligonucleotide.

3. The method according to claim 1, wherein the one or more oligonucleotides is present in a pharmaceutical composition.

4. The method according to claim 1, wherein the oligonucleotide comprises the nucleobase sequence of SEQ ID NO: 1.

5. The method according to claim 1, wherein the subject is also treated with another chemotherapeutic agent.

6. The method according to claim 5, wherein the another chemotherapeutic agent is a platinum-based chemotherapeutic agent, a taxane, a type I topoisomerase inhibitor, a type II topoisomerase inhibitor, or CHOP.

7. The method according to claim 5, wherein the another chemotherapeutic agent is Irinotecan or 5-fluoruracil.

8. The method according to claim 1, wherein the subject is also treated with chemoembolization, radiation, and/or surgical resection.

* * * * *

UNITED STATES PATENT AND TRADEMARK OFFICE
CERTIFICATE OF CORRECTION

| | | |
|---|---|---|
| PATENT NO. | : 11,034,959 B2 | |
| APPLICATION NO. | : 16/487355 | |
| DATED | : June 15, 2021 | |
| INVENTOR(S) | : Amriti R. Lulla and Wafik S. El-Deiry | |

It is certified that error appears in the above-identified patent and that said Letters Patent is hereby corrected as shown below:

In the Specification

Column 1, Line 3 immediately following the title, before the section entitled "FIELD" insert the following section heading and paragraph:
--STATEMENT OF GOVERNMENT SUPPORT
This invention was made with government support under CA176289, and CA006927 awarded by the National Institutes of Health. The government has certain rights in the invention.--

Signed and Sealed this
Fifth Day of September, 2023

Katherine Kelly Vidal
*Director of the United States Patent and Trademark Office*

```
                          SEQUENCE LISTING

<160> NUMBER OF SEQ ID NOS: 4

<210> SEQ ID NO 1
<211> LENGTH: 22
<212> TYPE: RNA
<213> ORGANISM: Homo sapien
<220> FEATURE:
<223> OTHER INFORMATION: hsa-miR-6883-5p

<400> SEQUENCE: 1
agggagggug ugguauggau gu                                             22

<210> SEQ ID NO 2
<211> LENGTH: 21
<212> TYPE: RNA
<213> ORGANISM: Homo sapien
<220> FEATURE:
<223> OTHER INFORMATION: hsa-miR-149-3p

<400> SEQUENCE: 2
agggagggac gggggcugug c                                              21

<210> SEQ ID NO 3
<211> LENGTH: 22
<212> TYPE: RNA
<213> ORGANISM: Homo sapien
<220> FEATURE:
<223> OTHER INFORMATION: hsa-miR-6785-5p

<400> SEQUENCE: 3
ugggagggcg uggaugaugg ug                                             22

<210> SEQ ID NO 4
<211> LENGTH: 23
<212> TYPE: RNA
<213> ORGANISM: Homo sapien
<220> FEATURE:
<223> OTHER INFORMATION: hsa-miR-4728-5p

<400> SEQUENCE: 4
ugggagggga gaggcagcaa gca                                            23
```